(12) United States Patent
Moaddeb et al.

(10) Patent No.: US 7,877,142 B2
(45) Date of Patent: Jan. 25, 2011

(54) METHODS AND SYSTEMS FOR CARDIAC REMODELING VIA RESYNCHRONIZATION

(75) Inventors: Shahram Moaddeb, Irvine, CA (US); Samuel M. Shaolian, Newport Beach, CA (US); Emanuel Shaoulian, Corona Del Mar, CA (US)

(73) Assignee: MiCardia Corporation, Irvine, CA (US)

( * ) Notice: Subject to any disclaimer, the term of this patent is extended or adjusted under 35 U.S.C. 154(b) by 633 days.

(21) Appl. No.: 11/773,311

(22) Filed: Jul. 3, 2007

(65) Prior Publication Data

US 2008/0051840 A1 Feb. 28, 2008

Related U.S. Application Data

(60) Provisional application No. 60/806,616, filed on Jul. 5, 2006.

(51) Int. Cl.
*A61N 1/362* (2006.01)
(52) U.S. Cl. .............................. 607/9; 600/16
(58) Field of Classification Search ....................... None
See application file for complete search history.

(56) References Cited

U.S. PATENT DOCUMENTS

| | | | |
|---|---|---|---|
| 4,354,497 A | | 10/1982 | Kahn |
| 4,925,443 A | * | 5/1990 | Heilman et al. ............... 600/16 |
| 4,928,688 A | | 5/1990 | Mower |
| 5,052,300 A | | 10/1991 | Josse |
| 5,174,289 A | | 12/1992 | Cohen |
| 5,176,618 A | | 1/1993 | Freedman |
| 5,267,560 A | | 12/1993 | Cohen |
| 5,403,356 A | | 4/1995 | Hill et al. |
| 5,514,161 A | | 5/1996 | Limousin |
| 5,584,867 A | | 12/1996 | Limousin et al. |
| 5,674,259 A | | 10/1997 | Gray |
| 5,720,768 A | | 2/1998 | Verboven-Nelissen |
| 5,792,203 A | | 8/1998 | Schroeppel |
| 5,797,970 A | | 8/1998 | Pouvreau |
| 5,902,324 A | | 5/1999 | Thompson et al. |
| 5,906,573 A | | 5/1999 | Aretz |
| 5,979,456 A | | 11/1999 | Magovern |

(Continued)

OTHER PUBLICATIONS

Calo-MER, "Shape-Memory Thermoplastic," Apr. 8, 2003, URL: http://www.polymertech.com/materials/calm5r.html, 4 pp., retrieved from the Internet May 18, 2005.

(Continued)

*Primary Examiner*—Kennedy J Schaetzle
(74) *Attorney, Agent, or Firm*—Aaron D. Barker; Stoel Rives LLP

(57) ABSTRACT

Systems, methods and devices are provided for improving the hemodynamic efficiency of a patient's heart by implanting one or more reinforcement elements on or with the heart and providing electrical stimulation to the heart. The reinforcement elements may include magnetic and/or shape memory material and are configured to reshape the heart so as to boost the heart's mechanical energy during a response to the electrical stimulation. In some embodiments, at least one reinforcement element includes an electrode configured to sense electrocardiogram signals within the heart. An electrical stimulation device such as an implantable or external pacemaker/defibrillator may be configured to control delivery of electrical pulses to the heart based on the sensed electrocardiogram signals. In addition, or in other embodiments, at least one reinforcement element includes an electrode configured to deliver the electrical pulses to the heart.

22 Claims, 27 Drawing Sheets

U.S. PATENT DOCUMENTS

| | | | |
|---|---|---|---|
| 6,045,497 A * | 4/2000 | Schweich et al. | 600/16 |
| 6,099,460 A * | 8/2000 | Denker | 600/17 |
| 6,123,724 A | 9/2000 | Denker | |
| 6,160,084 A | 12/2000 | Langer et al. | |
| 6,165,122 A | 12/2000 | Alferness | |
| 6,174,279 B1 | 1/2001 | Girard | |
| 6,193,648 B1 | 2/2001 | Krueger | |
| 6,332,863 B1 | 12/2001 | Schweich, Jr. et al. | |
| 6,332,864 B1 | 12/2001 | Schweich, Jr. et al. | |
| 6,388,043 B1 | 5/2002 | Langer et al. | |
| 6,402,679 B1 | 6/2002 | Mortier et al. | |
| 6,416,459 B1 | 7/2002 | Haindl | |
| 6,540,666 B1 | 4/2003 | Chekanov | |
| 6,564,094 B2 * | 5/2003 | Alferness et al. | 607/9 |
| 6,567,699 B2 | 5/2003 | Alferness et al. | |
| 6,587,734 B2 | 7/2003 | Okuzumi | |
| 6,595,912 B2 | 7/2003 | Lau et al. | |
| 6,602,184 B2 | 8/2003 | Lau et al. | |
| 6,604,529 B2 | 8/2003 | Kim | |
| 6,612,979 B2 | 9/2003 | Lau et al. | |
| 6,622,979 B2 | 9/2003 | Valiulis | |
| 6,629,921 B1 | 10/2003 | Schweich, Jr. et al. | |
| 6,645,139 B2 | 11/2003 | Haindl | |
| 6,663,558 B2 | 12/2003 | Lau et al. | |
| 6,673,009 B1 | 1/2004 | Vanden Hoek et al. | |
| 6,682,474 B2 | 1/2004 | Lau et al. | |
| 6,689,048 B2 | 2/2004 | Vanden Hoek et al. | |
| 6,702,732 B1 | 3/2004 | Lau et al. | |
| 6,720,402 B2 | 4/2004 | Langer et al. | |
| 6,723,038 B1 | 4/2004 | Schroeder et al. | |
| 6,723,041 B2 | 4/2004 | Lau et al. | |
| 6,746,471 B2 | 6/2004 | Mortier et al. | |
| 6,755,777 B2 | 6/2004 | Schweich, Jr. et al. | |
| 6,755,779 B2 | 6/2004 | Vanden Hoek et al. | |
| 6,959,214 B2 | 10/2005 | Pape et al. | |
| 7,186,210 B2 * | 3/2007 | Feld et al. | 600/16 |
| 7,285,087 B2 | 10/2007 | Moaddeb et al. | |
| 7,402,134 B2 * | 7/2008 | Moaddeb et al. | 600/37 |
| 2002/0065373 A1 | 5/2002 | Krishnan | |
| 2002/0161114 A1 | 10/2002 | Gunatillake et al. | |
| 2002/0188170 A1 | 12/2002 | Santamore et al. | |
| 2003/0078465 A1 * | 4/2003 | Pai et al. | 600/16 |
| 2003/0078671 A1 | 4/2003 | Lesniak et al. | |
| 2003/0100925 A1 | 5/2003 | Pape et al. | |
| 2003/0199974 A1 | 10/2003 | Lee et al. | |
| 2003/0233045 A1 | 12/2003 | Vaezy et al. | |
| 2004/0002626 A1 | 1/2004 | Feld et al. | |
| 2004/0014929 A1 | 1/2004 | Lendlein et al. | |
| 2004/0015187 A1 | 1/2004 | Lendlein et al. | |
| 2004/0098121 A1 | 5/2004 | Opolski | |
| 2004/0116945 A1 | 6/2004 | Sharkawy et al. | |
| 2004/0149290 A1 | 8/2004 | Nelson et al. | |
| 2004/0234453 A1 | 11/2004 | Smith | |
| 2004/0260393 A1 | 12/2004 | Rahdert et al. | |
| 2006/0015003 A1 | 1/2006 | Moaddes et al. | |
| 2006/0217774 A1 * | 9/2006 | Mower et al. | 607/9 |
| 2006/0276683 A1 | 12/2006 | Feld et al. | |

OTHER PUBLICATIONS

Cohen-Karni, Tzahi, "Fe-Pd Alloy Ferromagnetic Shape Memory Thin Films," Technion—Israel Institute of Technology, Harvard University, 2003, 31 pp.

Lendlein, Andreas et al., "Biodegradable, Elastic Shape-Memory Polymers for Potential Biomedical Applications," Science, vol. 296, May 31, 2002, pp. 1673-1676.

Li, Fengkui et al., "Studies on Thermally Stimulated Shape Memory Effect of Segmented Polyurethanes," J Appl Polym Sci (1997) 64: 1511-1516.

Tellinen, J. et al., "Basic Properties of Magnetic Shape Memory Actuators," Published in 8th International Conference Actuator, Germany, Jun. 2002, pp. 10-12.

Oikawa, Katsunari, "Development of Co-Ni-Al-based Ferromagnetic Shape Memory Alloys," AIST Today, vol. 1, No. 7, 2001, p. 18.

Notification of Transmittal of the International Search Report and The Written Opinion of the International Searching Authority, or the Declaration for International Application No. PCT/US2007/072786, filed Jul. 3, 2007.

* cited by examiner

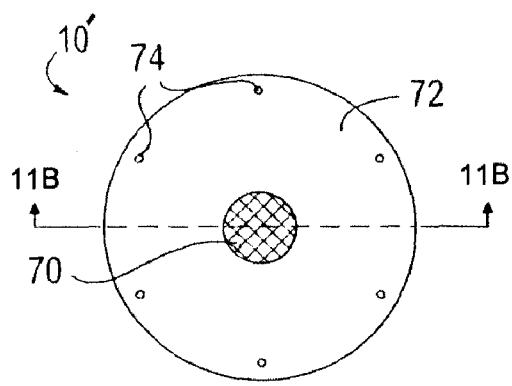 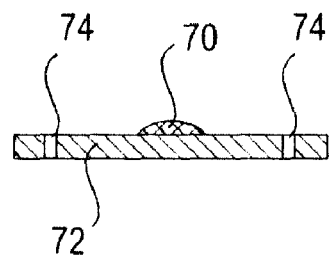
FIG. 11A          FIG. 11B
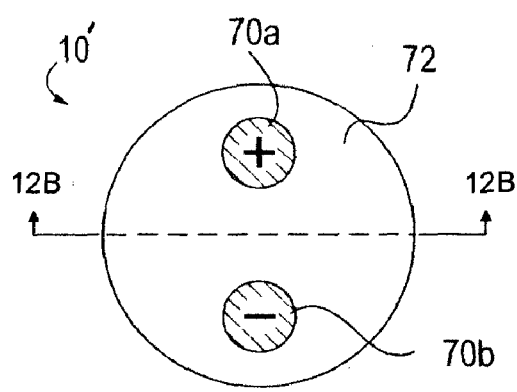 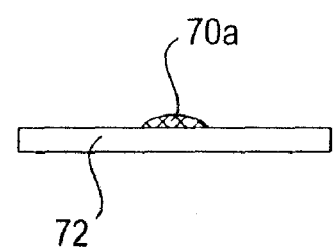
FIG. 12A          FIG. 12B
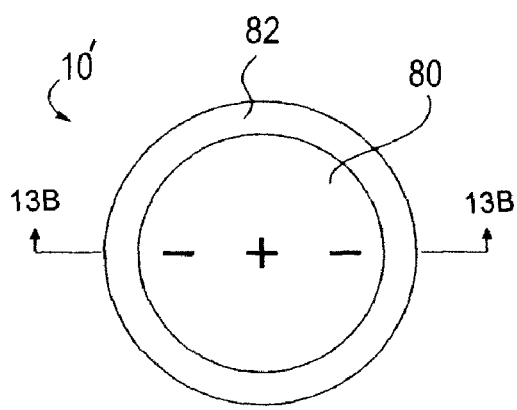 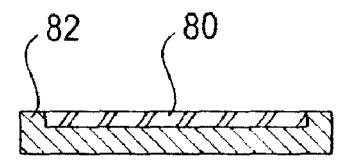
FIG. 13A          FIG. 13B

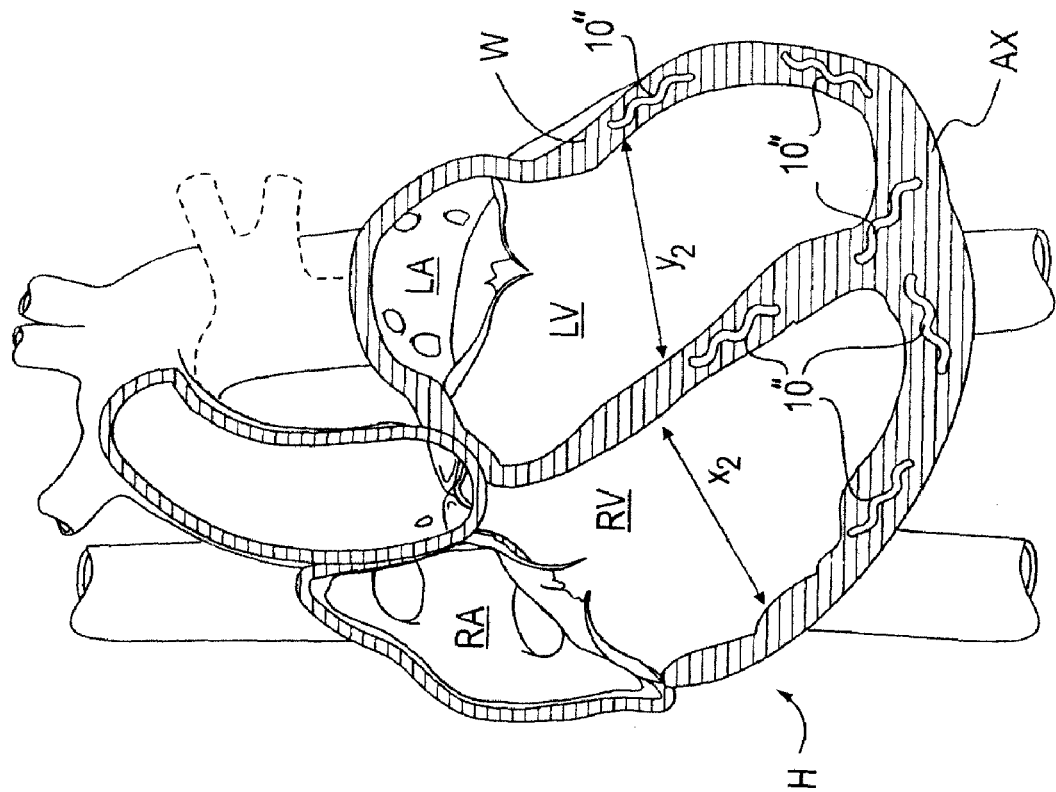
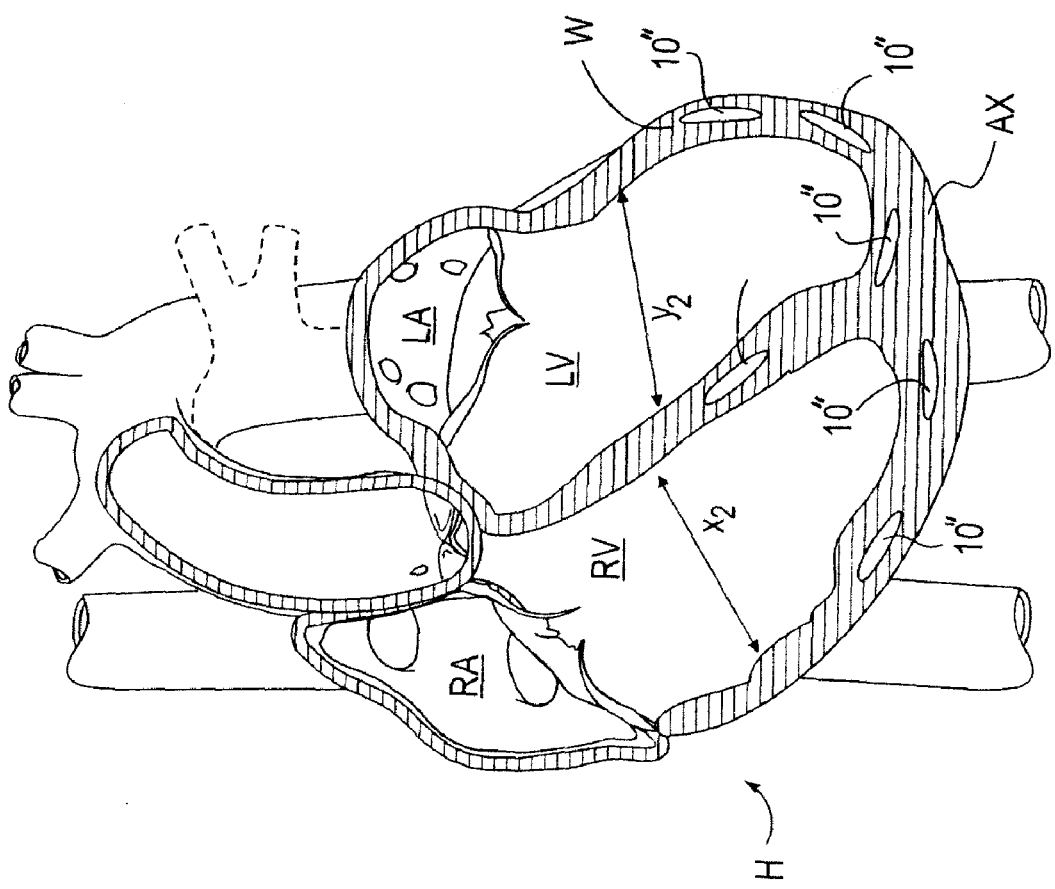

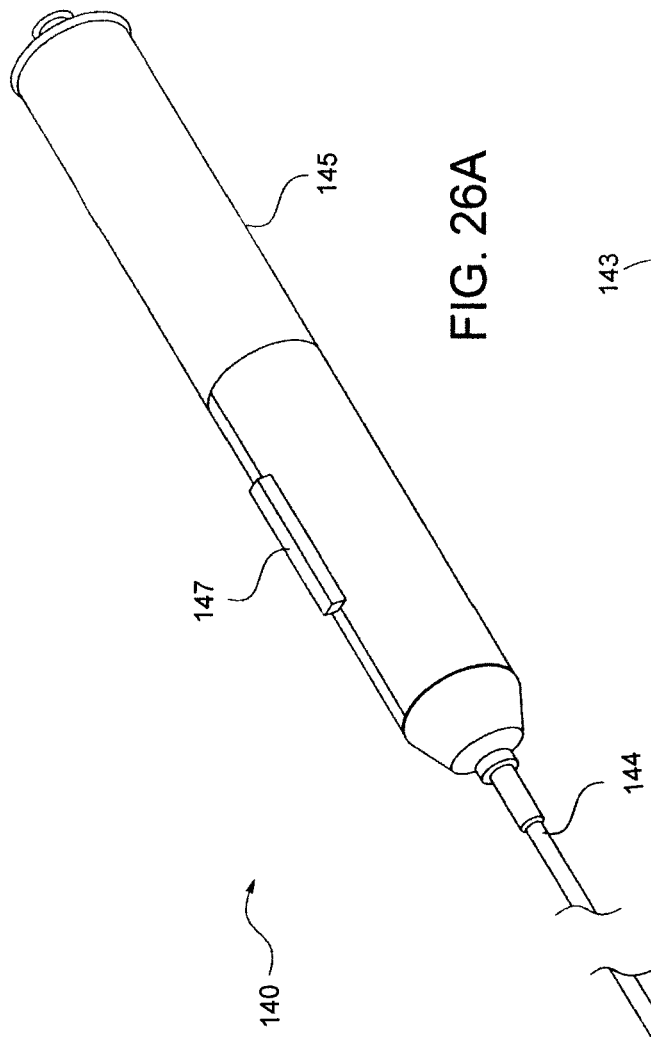
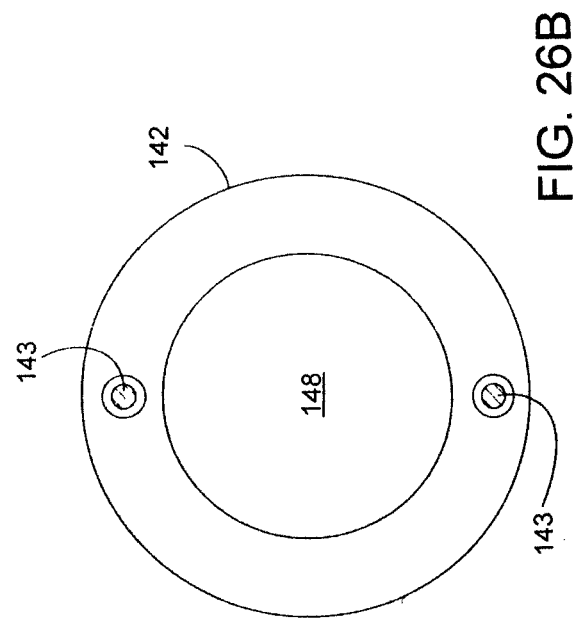
FIG. 26A
FIG. 26B

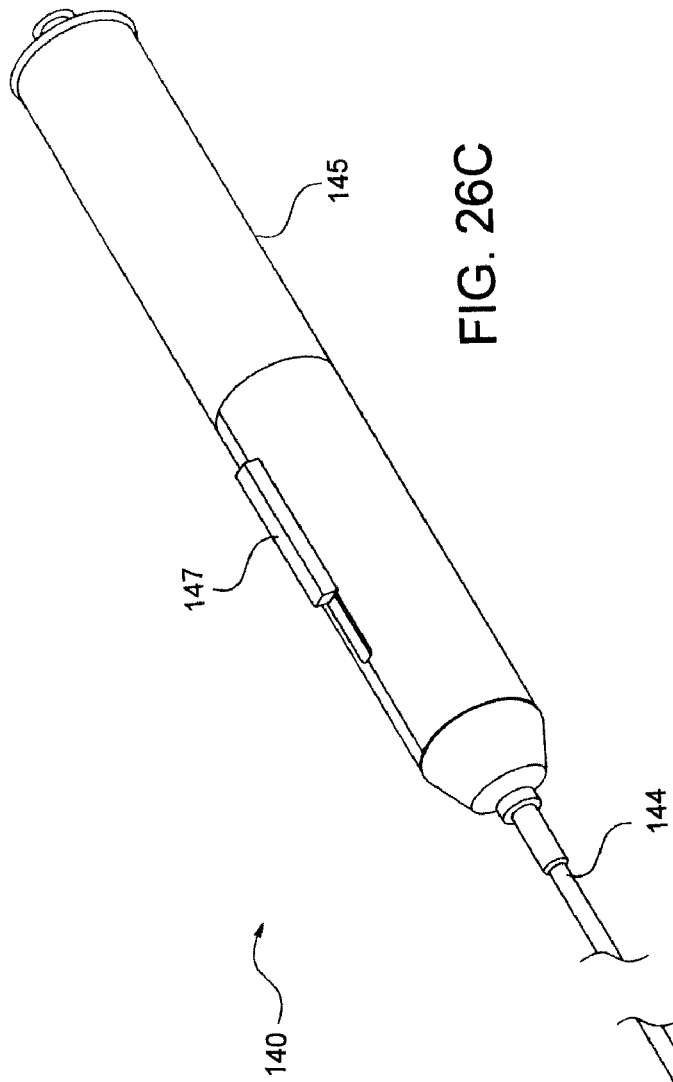

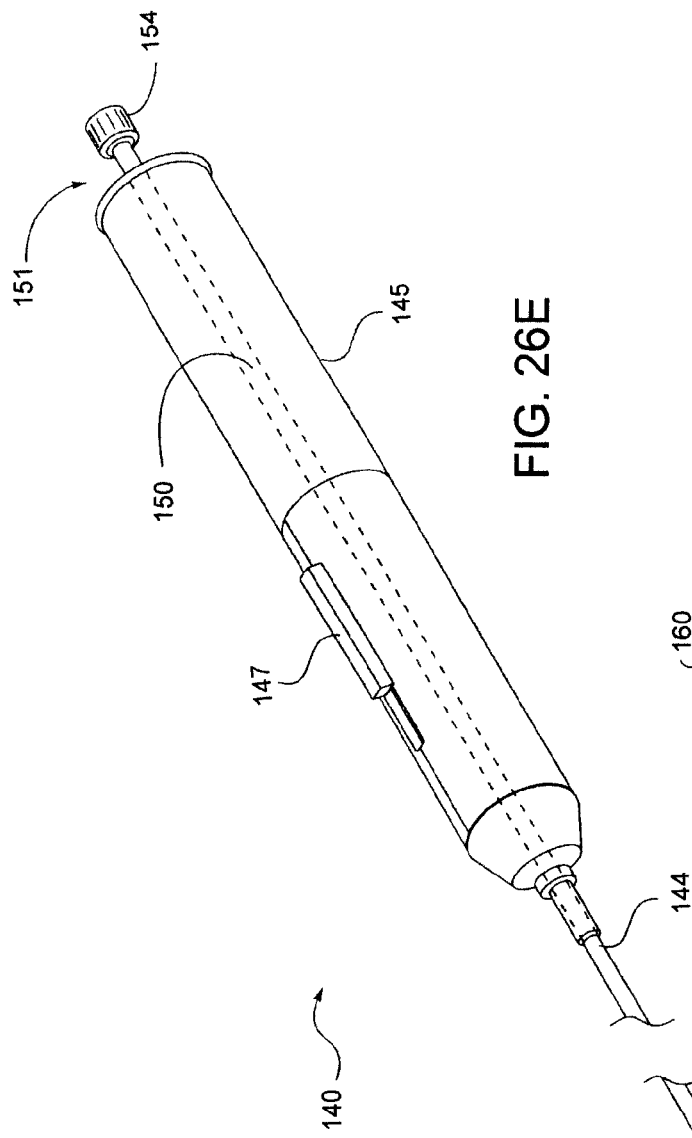
FIG. 26E
FIG. 26F

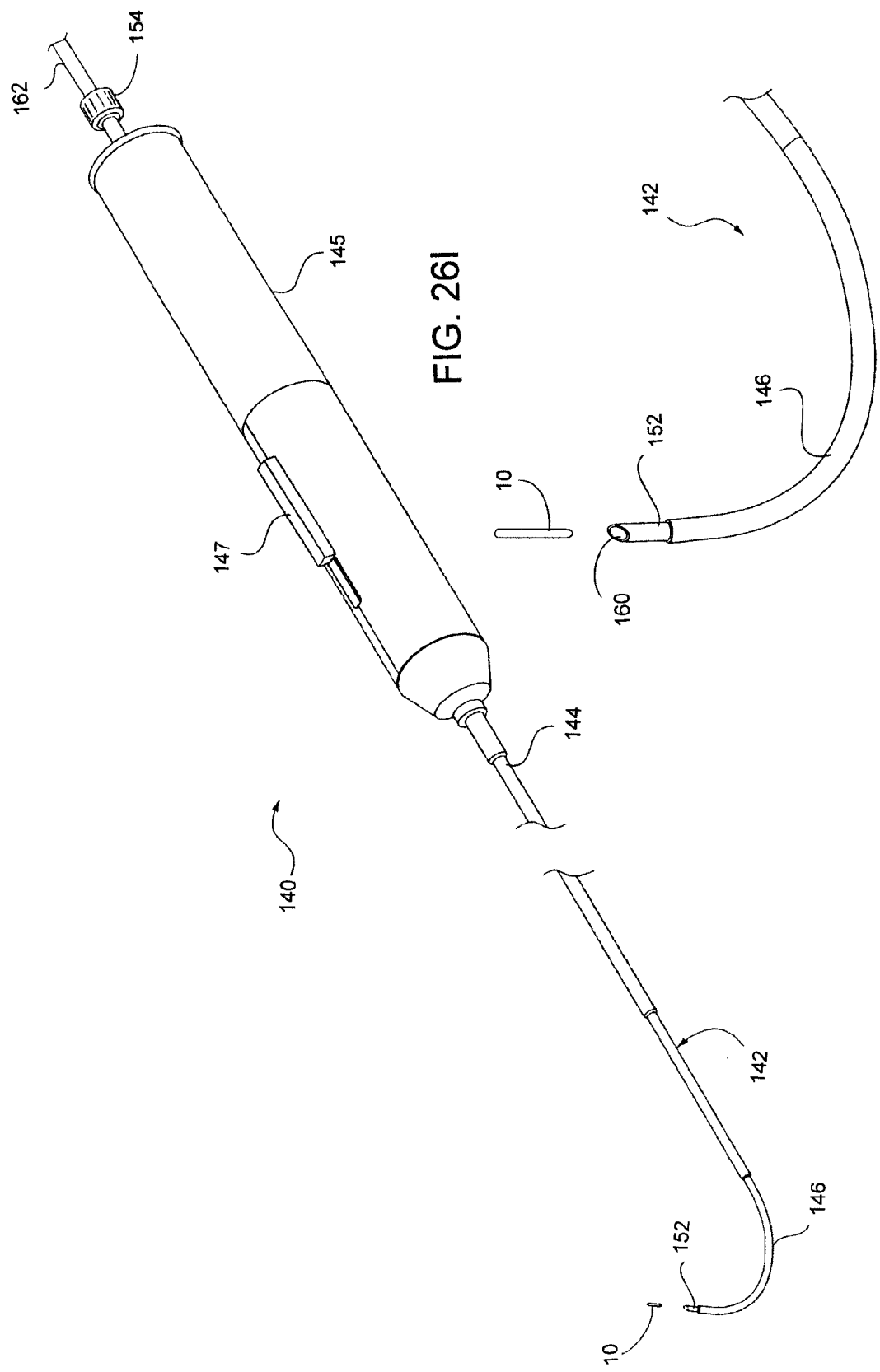

METHODS AND SYSTEMS FOR CARDIAC REMODELING VIA RESYNCHRONIZATION

RELATED APPLICATIONS

This application claims the benefit under 35 U.S.C. §119(e) of U.S. Provisional Application No. 60/806,616, filed Jul. 5, 2006, which is hereby incorporated by reference herein in its entirety.

TECHNICAL FIELD

This disclosure relates generally to cardiac stimulating devices. More particularly, this disclosure relates to implants that create mechanical booster energy to improve cardiac contraction, detect electrocardiogram signals within a heart, and/or deliver electrical stimulation energy to the heart.

BACKGROUND INFORMATION

Heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure, many of which are not fully known. In certain instances, heart disease may result from viral infections. In such cases, the heart may enlarge to such an extent that the adverse consequences of heart enlargement continue after the viral infection has passed and the disease continues its progressively debilitating course. In other cases, the initial cause is due to chronic hypertension, myocardial infarction, mitral valve incompetency, or other dilated cardiomyopathies. With each of these conditions, the heart is forced to overexert itself in order to provide the cardiac output demanded by the body during its various demand states. The result is dilation of the left ventricle and remodeling of the heart tissues.

Remodeling involves physical changes to the size, shape and thickness of the heart wall along with a neurohormonal milieu of the entire cardiovascular system. A damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. If dilation exceeds a critical value, the result will be progressive heart dilation which can be explained by Laplace's law. As the volume subtended by the left heart chamber increases, the stresses in the walls of this cavity will increase. Consequently, the muscle fibrils are overloaded and their ideal range of elongation is exceeded. When this excessive elongation takes place, there is a residual volume in the heart. Then the muscle fibrils must operate against a primarily high wall strain, and are further extended. A vicious cycle arises, leading to increasing distension of the heart and consequent heart insufficiency.

Heart transplantation is one surgical procedure used for treatment of heart failure. Unfortunately, not enough hearts are available for transplant to meet the needs of heart failure patients. In the United States, in excess of 35,000 transplant candidates compete for only about 2,000 transplants per year. A transplant waiting list is about 8-12 months long on average and frequently a patient may have to wait about 1-2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Consequently, substantial effort has been made to find alternative treatments for heart failure. One such surgical treatment is referred to as the Batista procedure; the surgical technique includes dissecting and removing portions of the heart in order to reduce heart volume. This is a radical and experimental procedure subject to substantial controversy. Furthermore, the procedure is highly invasive, risky and expensive and commonly includes other expensive procedures (such as a concurrent heart valve replacement). And if the procedure fails, emergency heart transplant is the only available option.

Another surgical treatment is dynamic cardiomyoplasty. In this procedure, the latissimus dorsi muscle (taken from the patient's shoulder) is wrapped around the heart and chronically paced synchronously with ventricular systole. Pacing of the muscle results in muscle contraction to assist the contraction of the heart during systole. Even though cardiomyoplasty has demonstrated symptomatic improvement, studies suggest the procedure only minimally improves cardiac performance. In addition, the procedure is highly invasive requiring harvesting a patient's muscle and an open chest approach (i.e., sternotomy) to access the heart. Furthermore, the procedure may be expensive and complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

A variety of devices have also been developed to treat heart failure by improving cardiac output. For example, left ventricular assist pumps have been developed to help the heart to pump blood. These mechanical pumps reduce the load on the heart by performing all or part of the pumping function normally done by the heart. Currently, mechanical pumps are used to sustain the patient while a donor heart for transplantation becomes available for the patient. Researchers and cardiac surgeons have also experimented with prosthetic "girdles" disposed around the heart. One such design is a prosthetic "sock" or "jacket" that is wrapped around the heart. However, these designs require invasive open chest surgery, significant handling of the heart, and have not seen widespread success.

Heart failure may also be caused by electrical conduction delay or blockage within the heart. For example, approximately 30% to approximately 50% of patients with congestive heart failure have interventricular conduction defects often in the pattern of a left bundle branch block (LBBB). These conduction abnormalities lead to a discoordinated contraction of an already failing and inefficient heart. Even a delayed activation of the left ventricle when the right ventricle alone is paced, for example, leads to significant dyssynchrony in left ventricular contraction and relaxation. The result is further deterioration of left ventricular performance because of abnormal septal motion, altered diastolic filling parameters, and alteration of heart geometry that may lead to worsening mitral regurgitation.

In recent years many new pacing and defibrillator devices with special algorithms have been proposed to alleviate heart failure conditions and restore synchronous depolarization and contraction of a single heart chamber or a combination of right/left and upper/lower heart chambers.

In patients who receive right-sided dual chamber pacemakers (e.g., pacemakers that include right atrial and right ventricular leads) for bradycardia indications, adjusting the timing intervals (e.g., in conjunction with echocardiographic Doppler filling characteristics) occasionally improves functional class (also referred to as New York Heart Association (NYHA) functional class) by optimizing cardiac output and diastolic filling parameters. Generally, however, attempts to resynchronize ventricular activation with traditional right sided pacing have not been very successful.

Strategies to correct dyssynchrony have led to technological advances in pacemaker therapy. Unlike traditional right-sided pacing, cardiac resynchronization devices may also use a left ventricular lead usually placed distally in the coronary sinus so that both ventricles are depolarized simultaneously. The synchronized activation improves overall cardiac function.

It has been proposed that biventricular pacing pulses be applied simultaneously to the right and left ventricles. Generally, the exact timing of mechanical events allows for properly controlling right and left heart chamber pacing so as to optimize left ventricular output. Specifically, it is known that actual contraction of one ventricular chamber before the other has the effect of moving the septum so as to impair full contraction in the later activated chamber. Thus, while concurrent or simultaneous pacing of the left and right ventricle may achieve a significant improvement for patients with congestive heart failure, it may be better to provide for pacing of the two ventricles in such a manner that the actual mechanical contraction of the left ventricle, with the consequent closing of the left valve, occurs in a desired time relationship with respect to the mechanical contraction of the right ventricle and closing of the right value. For example, if conduction paths in the left ventricle are impaired, delivering a pacing stimulus to the left ventricle at precisely the same time as delivering a pacing stimulus to the right ventricle may nonetheless result in left ventricular contraction being slightly delayed with respect to the right ventricular contraction.

Biventricular pacing includes traditional placement of a pacing lead in the right ventricle and placement of an additional pacing lead on the epicardial surface of the left ventricle. This is performed in an effort to resynchronize the contraction of the left ventricle. Placing a lead in the cavity of the left ventricle may result in complications due to thromboembolization, as thrombi frequently form on the surface of the left ventricle lead. Thus, to reduce or avoid thromboembolization, the left ventricle lead may be placed epicardially on the surface of the left ventricle.

In early use of biventricular pacing, the left ventricle leads were placed via a thoracotomy or through a thoracoscopy. Understandably these procedures may add significantly to the morbidity and mortality of already sick patients. Subsequently, a technique was developed that includes positioning a pacing wire on the surface of the left ventricle transvenously. The venous return from the myocardium includes multiple veins located on the surface of the heart that join to form the coronary sinus (CS). The CS then drains into the right atrium. It is possible to cannulate the CS from the right atrium and retrogradely place a pacing lead that is then positioned into one of its branches on the surface of the left ventricle.

Generally, however, conventional pacing systems require multiple lead placements. Further, due to an inability to directly stimulate the left heart, conventional pacing systems include high energy requirements that may cause early battery drainage with subsequent early battery replacement.

SUMMARY OF THE DISCLOSURE

Systems, methods and devices are provided for treating heart failure patients suffering from various levels of heart dilation. Heart dilation can be treated by reshaping the heart anatomy with the use of reinforcing elements to provide mechanical booster energy during electrical stimulation therapy. Such reshaping changes the geometry of portions of the heart, particularly the right or left ventricles, to increase contractibility of the ventricles thereby increasing the stroke volume which in turn increases the cardiac output of the heart. The reinforcement elements cause associated heart tissue areas to readjust position, such as to decrease the width of the ventricles. Such repositioning is maintained over time by the elements, allowing the damaging effects of heart dilation to slow in progression or reverse.

In one embodiment, a method is provided for improving the hemodynamic efficiency of a heart. The method includes attaching at least one reinforcement element to a tissue area of the heart, and electrically stimulating the heart. The at least one reinforcement element is configured to increase the heart's mechanical energy during a response to the electrical stimulation. In some embodiments, attaching at least one reinforcement element to a tissue of the heart comprises implanting at least one reinforcement element at least partially within a tissue area of the heart or to a surface of the heart.

The method may also include detecting electrocardiogram signals through the at least one reinforcement element, and based on the detected electrocardiogram signals, controlling delivery of an electrical impulse configured to provide the electrical stimulation. In addition, or in other embodiments, the method may also include delivering an electrical impulse through the at least one reinforcement element to provide the electrical stimulation the heart. The electrical impulses may be delivered based on a detected signal related to the mechanical motion of the heart.

In some embodiments, the at least one reinforcement element comprises at least one magnetic element that may include, for example, Neudynium Iron Boron, Samarium Cobalt, and/or Aluminum Nickel Cobalt. Such embodiments may include at least one outer layer comprising a non-magnetic material attached to the magnetic core.

In some embodiments, the at least one reinforcement element comprises at least one shape memory element that is transitionable between an original shape and at least one memory shape. The original shape may be configured for at least partial implantation within the tissue area of the heart, and the at least one memory shape may be configured to apply force to the tissue area to reshape the tissue area. The shape memory element may include, for example, at least one shape memory polymer, at least one shape memory metal or metal alloy, and/or at least one shape memory metal or metal alloy that exhibits a paramagnetic or ferromagnetic transition.

In another embodiment, a system for improving the hemodynamic efficiency of a heart includes an electrical stimulation device configured to deliver an electrical impulse to the heart, and at least one reinforcement element configured to increase the heart's mechanical energy during a response to the electrical impulse. The at least one reinforcement element may be implantable at least partially within a tissue area of the heart. In another embodiment the at least one reinforcement element may attach to a surface of the heart. The electrical stimulation device may include, for example, a pacemaker and/or defibrillator.

In some embodiments, the at least one reinforcement element includes an electrode electrically connected to the electrical stimulation device for delivering the electrical impulse to the heart.

In some embodiments, the system further includes diagnostic circuitry configured to analyze depolarizations within the heart. In certain such embodiments, the at least one reinforcement element further includes an electrode electrically connected to the diagnostic circuitry to sense the depolarizations within the heart. The electrical simulation device may be configured to stimulate the heart based on the sensed depolarizations and the diagnostic circuitry may be configured to coordinate at least one of an output signal magnitude and a rate of change of magnitude with heart contraction and ejection fraction values.

In another embodiment, a system includes means for electrically stimulating a patient's heart, and means for reshaping the heart to increase the heart's mechanical energy during a response to the electrical stimulation. The means for reshaping the heart may be configured to be implanted at least partially within a tissue of the heart. In some embodiments, the means for reshaping the heart is configured to sense depolarizations within the patient's heart. In certain such embodiments, the means for electrically stimulating the heart provides an electrical impulse based on the sensed depolarizations. In some embodiments, the means for reshaping the heart is configured to deliver an electrical impulse provided by the means for electrically stimulating the patient's heart.

Additional aspects and advantages will be apparent from the following detailed description of preferred embodiments, which proceeds with reference to the accompanying drawings.

BRIEF DESCRIPTION OF THE DRAWINGS

FIGS. 11A-11B, 12A-12B, and 13A-13B illustrate embodiments of magnetic elements including patches.

FIG. 18A illustrates shape memory elements in their original straight shape implanted within walls of the heart according to one embodiment.

FIG. 18B illustrates the shape memory elements of FIG. 18A transitioned to their memory folded shape while implanted within the walls of the heart according to one embodiment.

FIGS. 26A-26J illustrate an embodiment of a delivery system according to one embodiment.

DETAILED DESCRIPTION OF PREFERRED EMBODIMENTS

There is a need for alternative treatments applicable to both early and later stages of heart failure to correct pumping insufficiency due to distension of the heart thereby stopping the progressive nature of the disease or more drastically slowing the progressive nature of congestive heart disease. It is also desired that such therapies require minimal manipulation of the heart, be available to a broad spectrum of patients with various degrees of heart failure, be cost effective, safe and efficient. At least some of these objectives will be met with the embodiments disclosed herein.

As discussed above, there is also a need to treat interventricular conduction defects. Given the demonstrated feasibility of four-chamber cardiac pacing, and the availability of techniques for sensing natural cardiac signals and mechanical events, systems and methods are provided herein for adapting treatment of the cardiac condition of a patient with congestive heart failure so as to provide pacing sequences that are tuned for improving cardiac output, and in particular for improving left heart function.

In certain embodiments disclosed herein, permanent or removable implants create mechanical booster energy to improve cardiac contraction (e.g., improved ejection fraction (EF) and/or improved cardiac output (CO)). The implants may also provide simultaneous synchronization with implantable pulse generators for optimal or improved therapy according to individual patient needs. Combining mechanical booster energy with electrical cardiac stimulation reduces the number of leads and the amount of stimulation energy used to improve cardiac function. The added mechanical booster energy also increases battery longevity, which in turn reduces or minimizes the frequency of invasive battery replacement.

I. Reinforcement Elements

Figure 2:
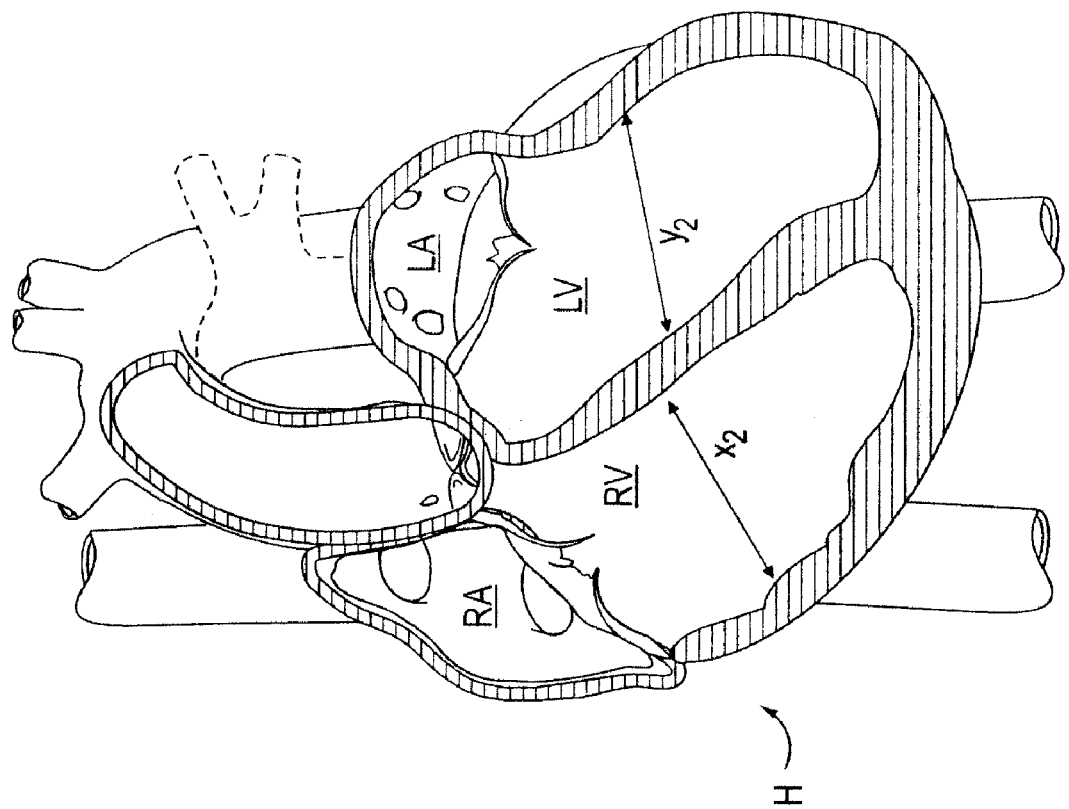
FIG. 2 provides a cross-sectional illustration of a heart of a patient wherein the geometry of the ventricles have dilated.
Figure 1:
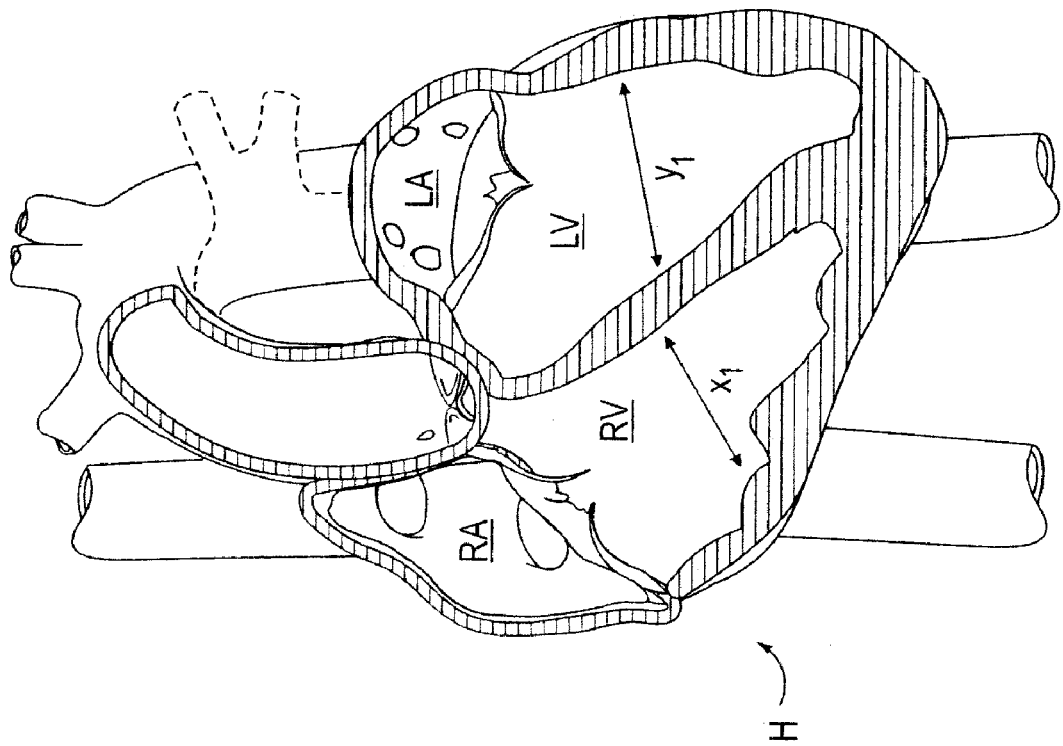
FIG. 1 provides a cross-sectional illustration of a heart of a normal patient.

FIG. 1 provides a cross-sectional illustration of a heart H of a normal patient. The cross-sectional view shows the right atrium RA, right ventricle RV, left atrium LA and left ventricle LV. The right ventricle RV and left ventricle LV have a width of $x_1$ and $y_1$ respectively. FIG. 2 provides a cross-sectional illustration of a heart H of a patient with heart disease wherein the geometry of the ventricles RV, LV have dilated. As shown, the right ventricle RV and left ventricle LV have increased widths of $x_2$ and $y_2$ respectively. The increased widths $x_2$, $y_2$ result in poor cardiac output from the left ventricle LV and/or the right ventricle RV. Cardiac output (CO) is defined as:

$$CO=HR \times SV,$$

whereas HR=heart rate (beats per minute) and SV=stroke volume (liters per beat). Ejection Fraction (EF) is the fraction of blood ejected by a ventricle relative to its end-diastolic volume. Therefore, EF is calculated from:

$$EF=(SV/EDV)*100,$$

whereas EDV=end-diastolic volume.

Ejection fraction is most commonly measured using echocardiography. This non-invasive technique provides good estimates of end-diastolic volume (EDV), end-systolic volumes (ESV), and stroke volume (SV=EDV−ESV). Normally, EF is >60%. For example, if the SV is 75 ml and the EDV is 120 ml, then the EF is 63%. Factors effecting EDV are heart rate, ventricular compliance and filling pressure. Factors effecting ESV are the force of contracting the left ventricle and after-load which is the measure of the force resulting from the ejection of blood.

In heart failure, particularly in dilated cardiomyopathy, EF can become very small as SV decreases and EDV increases. In severe heart failure, EF may be only 20% EF is often used as a clinical index to evaluate the status of the heart. By changing the geometry or reshaping the left or right ventricle with the methods and devices disclosed herein, the contractibility of the ventricles may be increased thereby increasing the stroke volume (SV). This in turn increases the cardiac output (CO).

Figure 3:
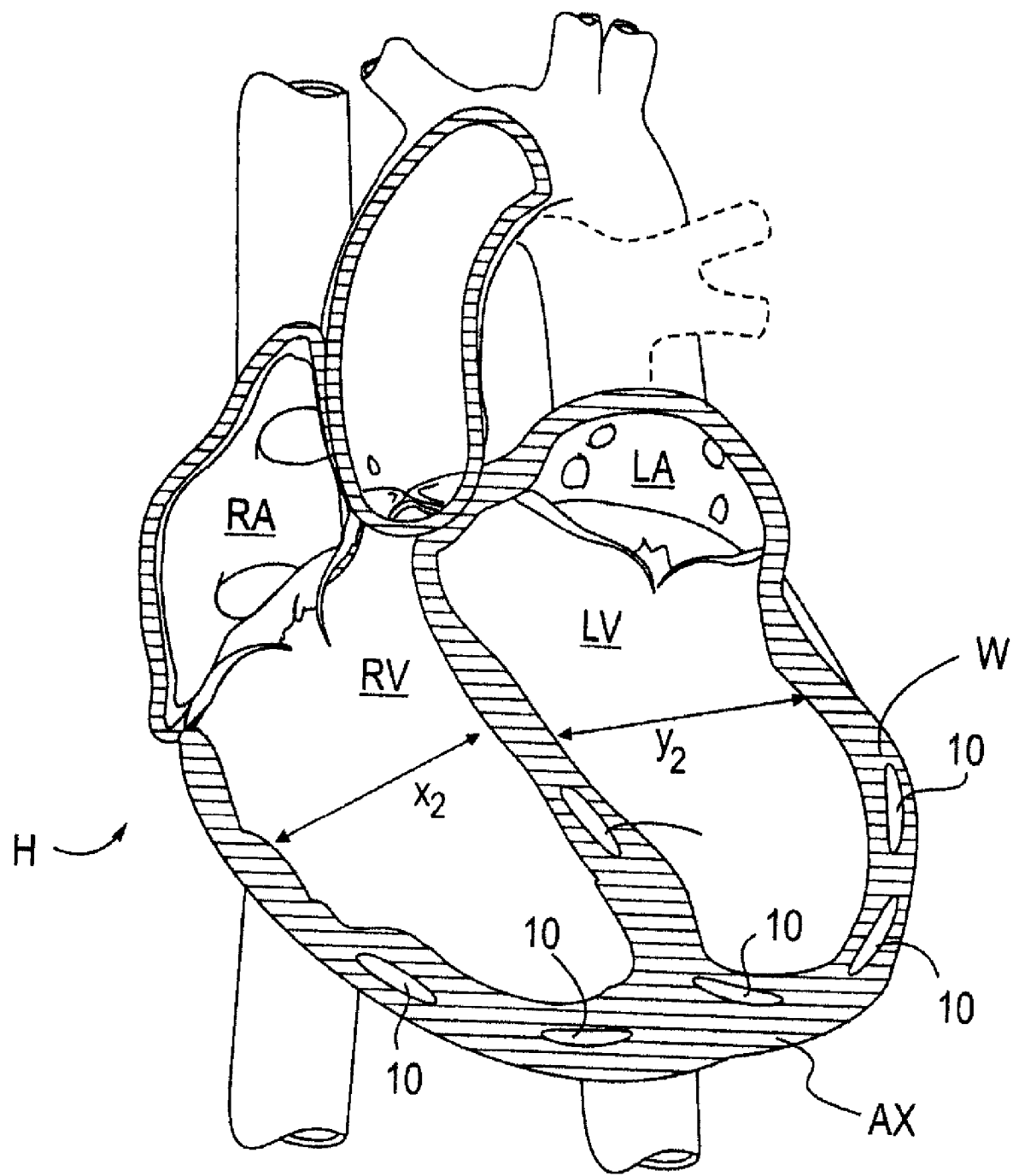
FIG. 3 provides a cross-sectional illustration of a heart of a patient wherein reinforcement elements have been placed according to one embodiment.

In certain embodiments disclosed herein, the geometry of the ventricles are changed by placing one or more reinforcement elements 10 on or within tissue areas or walls of the heart as illustrated in FIG. 3. In the embodiment of FIG. 3, reinforcement elements 10 are implanted within the walls W of the right ventricle RV and left ventricle LV near the apex AX of the heart H. The reinforcement elements 10 are designed to provide additional forces that draw the walls W of the ventricles RV, LV inward, toward each other, thereby reshaping the ventricles RV, LV. The width of the right ventricle RV is thus reduced toward normal width $x_1$ and the left ventricle LV is reduced toward the normal width $y_1$. The forces provided by the reinforcement elements 10 are able to assist the ventricles RV, LV throughout the cardiac cycle, increasing the contractibility of the ventricles RV, LV. This increases the stroke volume (SV) which increases the cardiac output (CO). It may be appreciated that any number of reinforcement elements 10 may be used and that the reinforcement elements 10 may be positioned at any location on (externally or internally) or within the walls W of the heart H, including the right atrium RA, right ventricle RV, left atrium LA and left ventricle LV. It may further be appreciated that the reinforcement elements 10 may be positioned on or within the valves, including the mitral valve MV, aortic valve AV, tricuspid valve TV, and pulmonary valve (not shown), and/or any of the associated anatomy, such as the aorta A, pulmonary artery, pulmonary vein, chordae etc.

When the reinforcement elements 10 are positioned within the walls W, the reinforcement elements 10 are advanced through at least a portion of the wall W with the use of a delivery instrument, as will be described below, so that the reinforcement elements 10 are substantially surrounded by the tissue of the walls W and therefore held in place by the tissue of the walls W. When the reinforcement elements 10 are positioned on the walls W, the elements 10 are held in place by adhesion to the surface of the walls W or by anchoring into the walls W, such as by suturing or advancing one or more protrusions into the walls W.

As discussed in further detail below, in some embodiments, the reinforcement elements 10 are used with an electrical stimulation device such as a pacemaker and/or defibrillator. In such embodiments, the reinforcement elements 10 may be configured to detect electrocardiogram signals and/or deliver electrical impulses to a patient's heart. In some embodiments, the reinforcement elements 10 include coatings and/or coverings and may comprise magnetic and/or shape memory materials configured to reshape at least a portion of a patient's heart.

A. Coatings/Coverings

The reinforcement elements 10 of the disclosed embodiments may include a variety of coatings or coverings. The coatings or coverings may be present in any number and in any combination.

In some embodiments, the reinforcement elements 10 are covered with a lubricious coating for ease of placement, both within a delivery device and within the tissue. Examples of lubricious coatings include polytetrafluoroethylene and coated silicone (silicone having a treated surface which provides low surface tension), to name a few.

In some embodiments, the reinforcement elements 10 are covered with an anti-inflammatory coating to minimize any potential inflammatory response by the tissue. Examples of anti-inflammatory coatings include dexamethasone sodium phosphate and dexamethasone acetate, to name a few.

In some embodiments, the reinforcement elements 10 are covered with a biocompatible jacket or sleeve. Such a jacket or sleeve reduces any potential immunological response by the tissue to a reinforcement element 10 comprised of a less-biocompatible foreign material. Further, such a jacket or sleeve may ease removal of the reinforcement element 10 from a location, such as the coronary sinus, post implant or once physical remodeling has taken place (generally within 6-12 months). In some embodiments, the biocompatible jacket or sleeve is comprised of ePTFE or Teflon®.

In some embodiments, the reinforcement elements 10 are porous or are coated with a porous coating. It may be appreciated that porous includes microporous wherein microporous materials are solids that contain interconnected pores of molecular dimensions (i.e. <2 nm). Porosity increases the surface area of the reinforcement element 10 which may improve thermal conduction and heat transfer properties. Porous materials may include metals, ceramics, or polymers, to name a few. Example coatings include carbon, graphite, titanium nitrite, titanium carbite, iridium oxide and conductive porous polymers.

The reinforcement elements 10 may also be used to deliver various agents, such as anti-calcification or anti-inflammatory drugs. In some embodiments, the agents are eluted from pores of a porous surface of the reinforcement element 10. In other embodiments, the reinforcement element 10 includes a controlled-release material impregnated with the agent, wherein the rate controlling material controls the rate at which the agent is released. Controlled-release or rate-controlled materials deliver an agent at a predetermined rate. Such delivery may be achieved by a number of methods.

First, the agent may be released by diffusion through the controlled-release material. In this case, the agent is typically present as finely dispersed particles in a polymer matrix membrane. This is often termed a monolithic dispersed type system, monolithic device, or matrix diffusion system. As the concentration of agent is reduced in the matrix due to diffusion delivery, the slope of the drug diffusion curve is also reduced. The agent delivery rate decreases over time as the material is depleted. Hence, the characteristic release profile of a monolithic system follows an asymptotic curve; after an initial burst of rapid release, the elution approaches a constant rate.

Second, the agent may be released by degradation of the controlled-release material. The agent may be encapsulated or contained in a biodegradable material and any number of degradation rates may be achieved by manipulating the composition of the material. Further, the agent may be released by a combination of diffusion and degradation. And, as mentioned, alternatively or in addition, the agent may be released by elution from pores. If the agent is contained in a controlled-release material which fills the pores, the agent may be released from the controlled-release material by diffusion and/or degradation and then elution from the pores themselves.

B. Magnetic Reinforcement Elements

Figure 4:
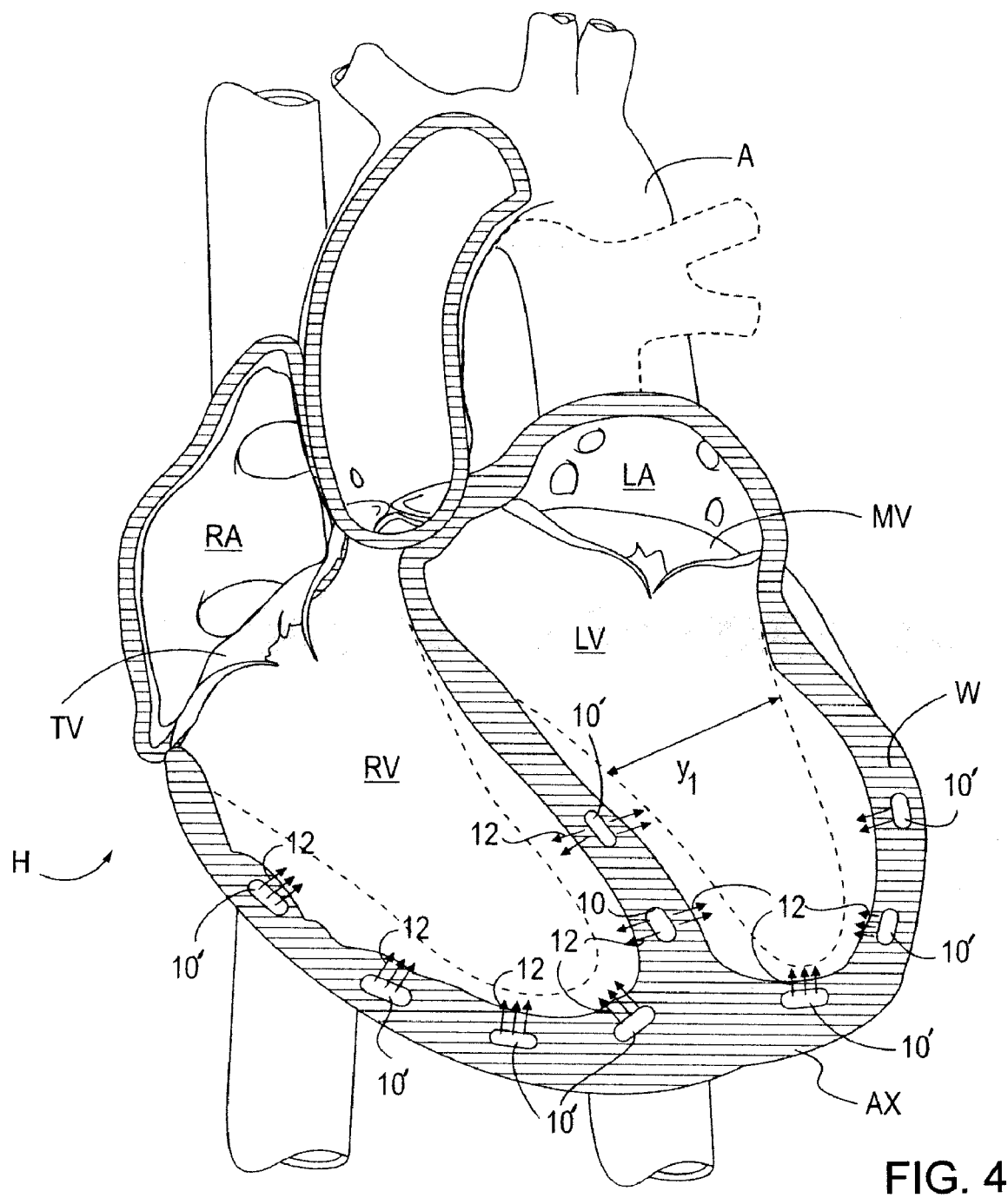
FIG. 4 illustrates changing of the geometry of the ventricles of FIG. 2 by placing magnetic elements within the walls of the ventricles according to one embodiment.

In one embodiment, the reinforcement elements 10 include magnetic material and the geometry of the ventricles is changed by placing the magnetic reinforcement elements 10 (referred to herein as magnetic elements 10') on or within tissue areas or walls W of the ventricles, such as illustrated in FIG. 4. In the embodiment of FIG. 4, magnetic elements 10' are implanted within the walls W of the right ventricle RV and left ventricle LV near the apex AX of the heart H. The magnetic elements 10' have opposing poles so that the magnetic elements 10' attract each other, as indicated by arrows 12. Such attraction draws the walls W of the ventricles RV, LV inward, toward each other, thereby reshaping the ventricles RV, LV. The width of the right ventricle RV is thus reduced toward normal width $x_1$ and the left ventricle LV is reduced toward the normal width $y_1$. The magnetic forces are able to assist the ventricles RV, LV throughout the cardiac cycle, increasing the contractibility of the ventricles RV, LV.

Figure 5A:
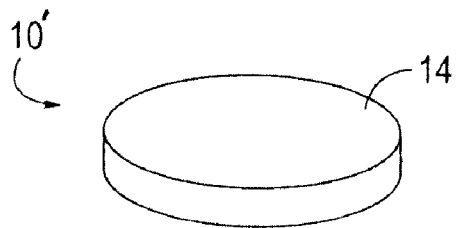
FIGS. 5A-5C illustrate a magnetic disc according to one embodiment.
Figure 5B:
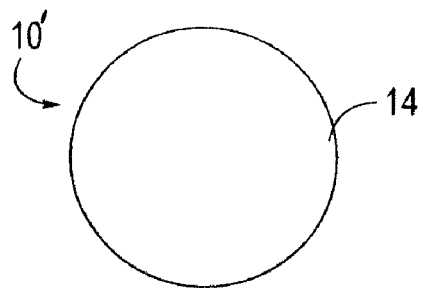
Figure 5C:
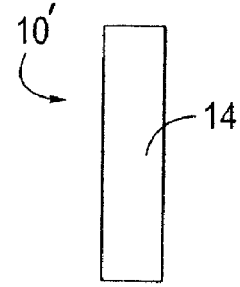

The magnetic elements 10' are comprised of any suitable magnetic material, such as Neudynium Iron Boron (Nd Fe B), Samarium Cobalt (Sm Co) or Aluminum Nickel Cobalt (Al Ni Co). The magnetic elements 10' may have any suitable size and shape, including discs, cones, rods, blocks, spheres, and rings to name a few. In one embodiment, illustrated in FIGS. 5A-5C, a magnetic element 10' has the shape of a disc 14. FIG. 5A provides a perspective view of the magnetic disc 14. FIG. 5B illustrates a top view having a circular shape with a diameter in the range of approximately 0.1-3 mm. FIG. 5C illustrates a side view wherein the disc 14 has a thickness in the range of approximately 0.1-3 mm. These magnetic discs 14 can provide forces in the range of approximately 0.2-0.5 lbf with a magnetic field in the range of 300-7000 Gauss. In addition, the discs 14 may be coated with a biocompatible polymer, such as polyurethane, polytetrafluoroethylene (PTFE), fluorinated ethylene propylene (FEP) or polyether ether ketone (PEEK). Typically, such a coating has a thickness in the range of approximately 0.1-0.3 mm.

Figure 6A:
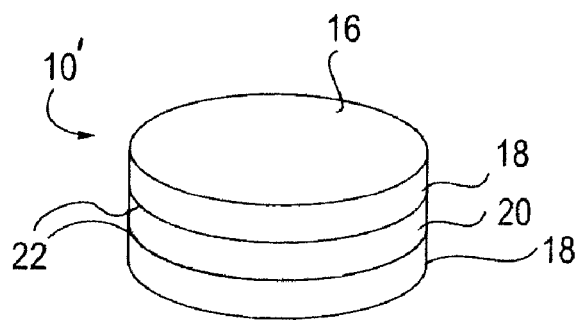
FIGS. 6A-6C illustrate a magnetic disc according to another embodiment.
Figure 6B:
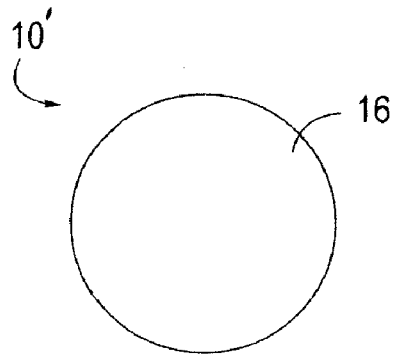
Figure 6C:
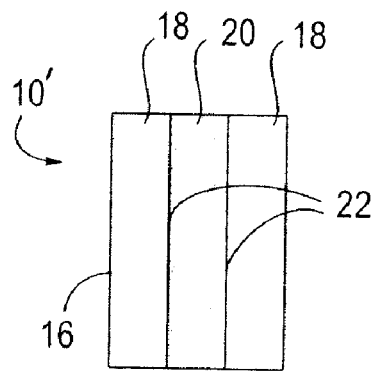

In another embodiment, illustrated in FIGS. 6A-6C, a magnetic element 10' has the form of a composite magnetic disc 16. Here, the composite magnetic disc 16 is comprised of a core inner layer 20 and two outer layers 18. The core inner layer 20 is comprised of any suitable magnetic material, such as Neudynium Iron Boron (Nd Fe B), Samarium Cobalt (Sm Co) or Aluminum Nickel Cobalt (Al Ni Co), and has a thickness in the range of approximately 0.1-3 mm. The outer layers 18 are comprised of any suitable non-magnetic material, such as 316L stainless steel, and have a thickness of approximately 0.1 mm. The outer layers 18 are joined with the core inner layer 20 with a suitable adhesive 22, such as cyanoacrylate or epoxy.

FIG. 6A provides a perspective view of the composite magnetic disc 16. FIG. 6B illustrates a top view having a circular shape with a diameter in the range of approximately 0.1-3 mm. FIG. 6C illustrates a side view wherein the disc 16 has a thickness in the range of approximately 0.1-3 mm. The composite magnetic discs 16 provide a less brittle magnet and an increased force of attraction. In addition, the discs 16 may also be coated with a biocompatible polymer, such as polyurethane, polytetrafluoroethylene (PTFE), fluorinated ethylene propylene (FEP) or polyether ether ketone (PEEK). Typically, such a coating has a thickness in the range of approximately 0.1-0.3 mm.

It may be appreciated that the disclosed magnetic elements 10' may have the form of a rod. In some embodiments, the rod has a diameter in the range of approximately 0.1-3 mm and a length in the range of 3-8 mm. Similar to the magnetic discs described above, the rod may be comprised of any suitable magnetic material, such as Neudynium Iron Boron (Nd Fe B), Samarium Cobalt (Sm Co) or Aluminum Nickel Cobalt (Al Ni Co), to name a few. Likewise, the rod may include a biocompatible polymer coating 34 (see FIGS. 7A-7C), such as polyurethane, polytetrafluoroethylene (PTFE), fluorinated ethylene propylene (FEP) or polyether ether ketone (PEEK), having a thickness in the range of 0.1-0.3 mm.

Figure 7A:
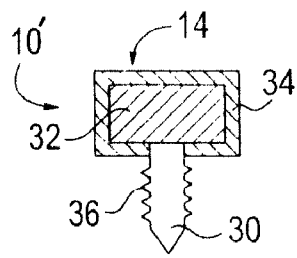
FIGS. 7A-7C illustrate magnetic elements having protrusions for anchoring according to certain embodiments.
Figure 7B:
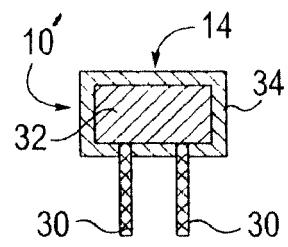
Figure 7C:
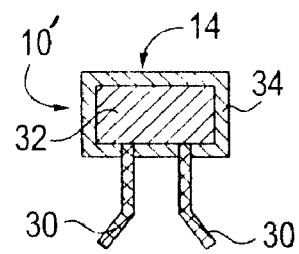

The magnetic elements 10' may be positioned at any location on (externally or internally) or within the walls W of the heart H. When the magnetic elements 10' are positioned within the walls W, the magnetic elements 10' are advanced through at least a portion of the wall W with the use of a delivery instrument, as will be described in later sections, so that the magnetic elements 10' are substantially surrounded by the tissue of the walls W and therefore held in place by the tissue of the walls W. When the magnetic elements 10' are positioned on the walls W, the magnetic elements 10' are held in place by adhesion to the surface of the walls W or by anchoring into the walls W, such as by suturing or advancing one or more protrusions into the walls W. For example, FIGS. 7A-7C illustrate embodiments of magnetic elements 10' having protrusions 30 suitable for advancement into the walls W. In the embodiment shown in FIG. 7A, the magnetic element 10' comprises a magnetic disc 14, such as the magnetic disc 14 of FIGS. 5A-5C having a core 32 of suitable magnetic material, and a protrusion 30 having the shape of a screw. The screw shape includes threads 36 so that the protrusion 30 may be advanced through the tissue of the ventricle wall W and held in place. The disc 14 and protrusion 30 may be joined by any suitable means, such as by an adhesive or a mechanical attachment mechanism. It may also be appreciated that the disc 14 and protrusion 30 may be formed as a continuous unit. The disc 14 is also typically covered by a biocompatible polymer coating 34, such as polyurethane, polytetrafluoroethylene (PTFE), fluorinated ethylene propylene (FEP) or polyether ether ketone (PEEK). The protrusion 30 may be comprised of any suitable material, such as stainless steel. Further, the protrusion 30 may be plated or coated with a material to provide desired physical characteristics. For example, if the disc 14 and protrusion 30 are formed as one unit of magnetic material, the protrusion 30 may be coated with stainless steel to reduce brittleness. It may also be appreciated that magnetic discs 14 of any shape and composition may have protrusions 30, including the magnetic disc 16 of FIGS. 6A-6C.

Figure 8:
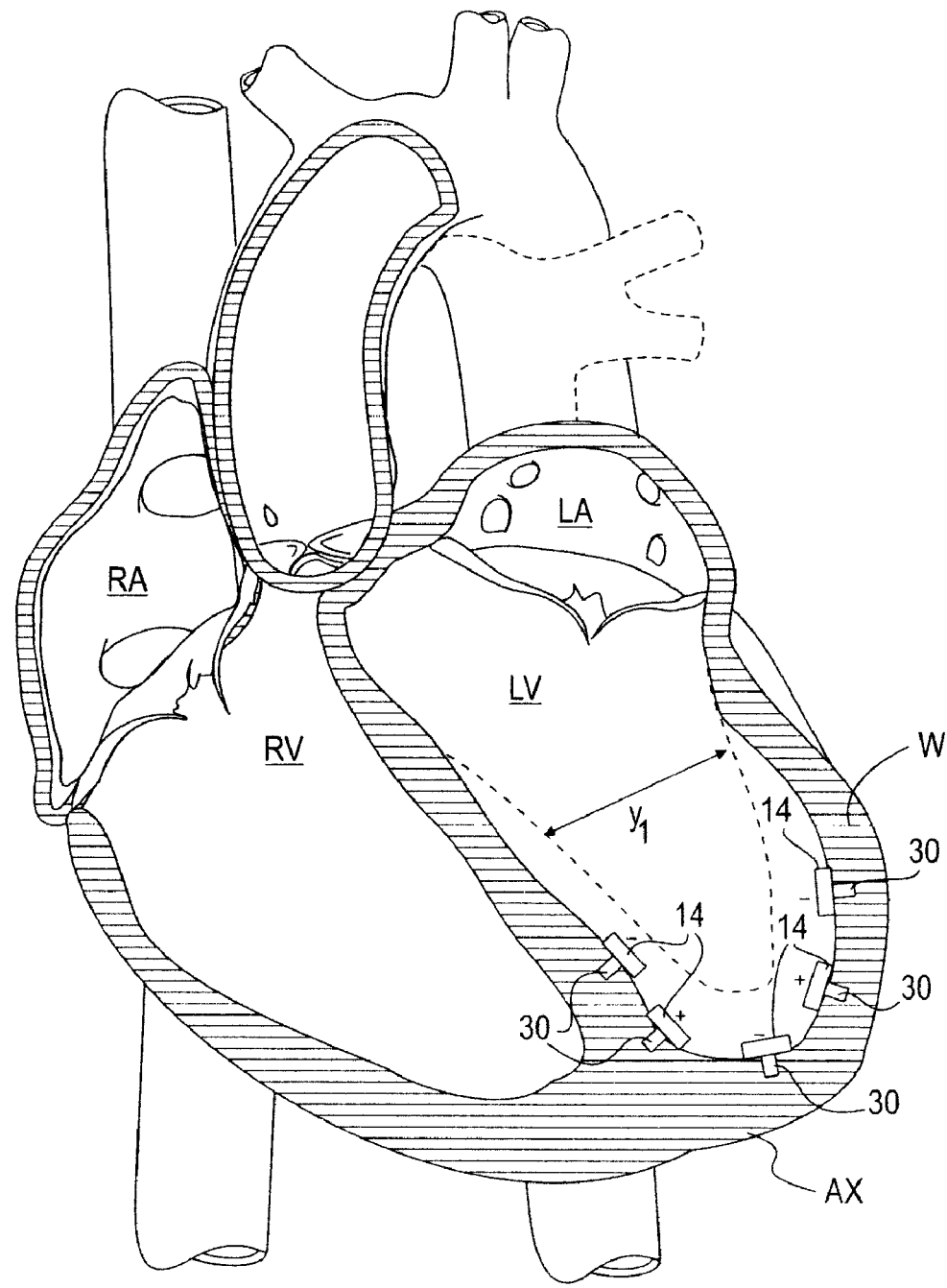
FIG. 8 illustrates magnetic elements having protrusions anchored to the walls of the left ventricle according to one embodiment.

Referring to FIG. 8, magnetic elements 10' having protrusions 30 are illustrated anchored to the walls W of the left ventricle LV. Here, five magnetic elements 10' are shown near the apex AX of the heart H. The protrusions 30 are advanced into the ventricular tissue of the walls W so that the discs 14 are disposed on the interior surface of the left ventricle LV. The magnetic elements 10' have opposing poles so that the magnetic elements 10' attract each other. Such attraction draws the walls W of the left ventricle LV inward, toward each other, thereby reshaping the left ventricle LV. The width of the left ventricle LV is thus reduced toward the normal width $y_1$. The magnetic forces are able to assist the left ventricle LV throughout the cardiac cycle, increasing the contractibility of the LV ventricle. This increases the stroke volume (SV) which increases the cardiac output (CO).

Additional embodiments of magnetic elements 10' having protrusions 30 for anchoring are shown in FIGS. 7B-7C. In FIG. 7B, a magnetic element 10' comprises a magnetic disc 14, such as the magnetic disc 14 of FIGS. 5A-5C having a core 32 of suitable magnetic material, and at least one protrusion 30. The protrusions 30 are directly advanceable into the ventricular tissue of the wall W. To hold the magnetic elements 10' in place, the protrusions 30 are then curved, bowed or bent, as illustrated in FIG. 7C. Such bending may be achieved by a variety of mechanisms. For example, the protrusions 30 may be comprised of a shape memory material, such as Nickel Titanium (also known as Nitinol®), wherein the change in shape is achieved by applying an electrical current, such as a DC voltage or radiofrequency, or by applying external energy, such as a magnetic field using a clinically available magnetic resonance imaging machine or high intensity focused ultrasound. Such application raises the temperature of the shape memory material from 37° C. to a transition temperature of 45-50° C. wherein bending occurs. The bent protrusion 30 thus anchors the magnetic element 10' to the wall W. Again, the disc 14 and protrusions 30 may be joined by any suitable means, such as by an adhesive or a mechanical attachment mechanism. It may also be appreciated that the disc 14 and protrusions 30 may be formed as a continuous unit. The disc 14 is also typically covered by a biocompatible polymer coating 34, such as polyurethane, polytetrafluoroethylene (PTFE), fluorinated ethylene propylene (FEP) or polyether ether ketone (PEEK). It may further be appreciated that the magnetic element 10' may have the form of a composite disc 16 such as illustrated in FIGS. 6A-6C. Or the magnetic element 10' may have any other form including cones, rods, blocks, spheres and rings, to name a few.

Figure 9A:
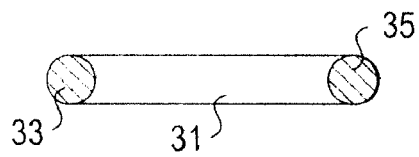
FIGS. 9A-9B illustrate magnetic elements joined by a tether according to one embodiment.
Figure 9B:
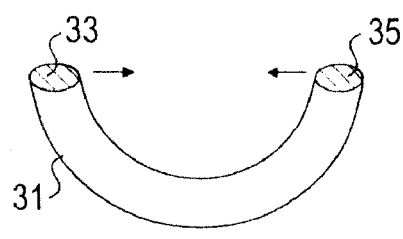
Figure 9C:
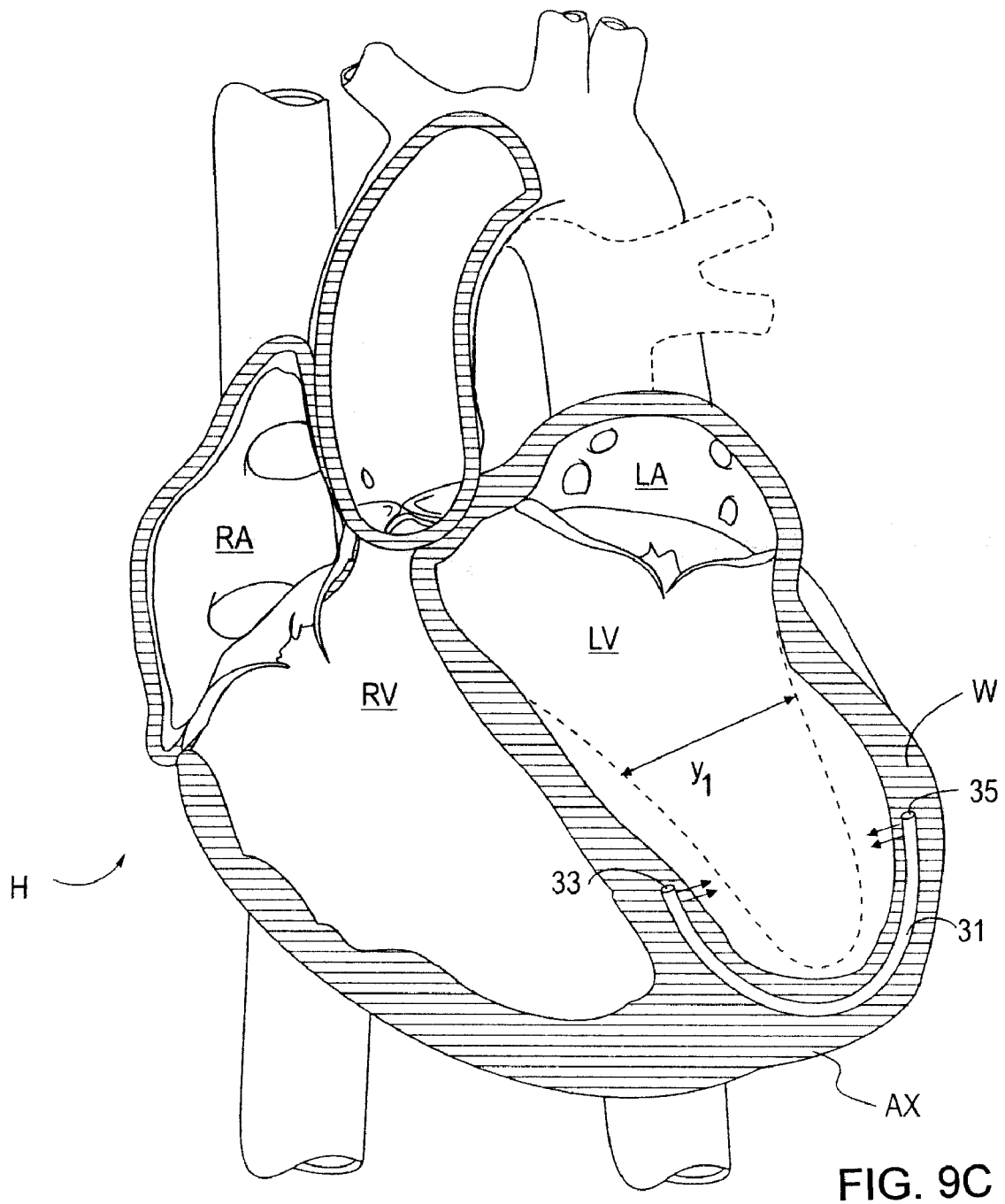
FIG. 9C illustrates the magnetic elements of FIGS. 9A-9B implanted within the wall of the left ventricle according to one embodiment.

In still further embodiments, the magnetic elements 10' are joined by a tether 31, as illustrated in FIGS. 9A-9B. Referring to FIG. 9A, a first magnetic element 33 is connected to one end of the tether 31 and a second magnetic element 35 is connected with the other end of the tether 31. The tether 31 may be comprised of any flexible material, such as a polymer, wire, filament, thread, suture, braid, coil, or mesh, to name a few. The tether 31 may be elastic or non-elastic. Further, the tether 31 may be bioabsorbable, such as comprised of polyglycolic acid (PGA). FIG. 9A shows the tether 31 in a substantially straight configuration. Magnetic elements 33, 35 having opposite charges are magnetically attracted to each other causing the tether 31 to curve, as shown in FIG. 9B. Referring to FIG. 9C, a tether 31 is shown implanted in the wall W of the left ventricle LV near the apex AX of the heart H so that magnetic elements 33, 35 are positioned on opposite sides of the left ventricle LV. Opposite charges on the first magnetic element 33 and second magnetic element 35 cause magnetic attraction. Such attraction draws the walls W of the left ventricle LV inward, toward each other, thereby reshaping the left ventricle LV. The width of the left ventricle LV is thus reduced toward the normal width $y_1$. In addition, the tether 31 pulls the wall W between the elements 33, 35 near the apex AX upward and inward as the elements 33, 35 attract. Thus, the magnetic forces are able to assist the left ventricle LV throughout the cardiac cycle, increasing the contractibility of the left ventricle LV. This increases the stroke volume (SV) which increases the cardiac output (CO).

Figure 10:
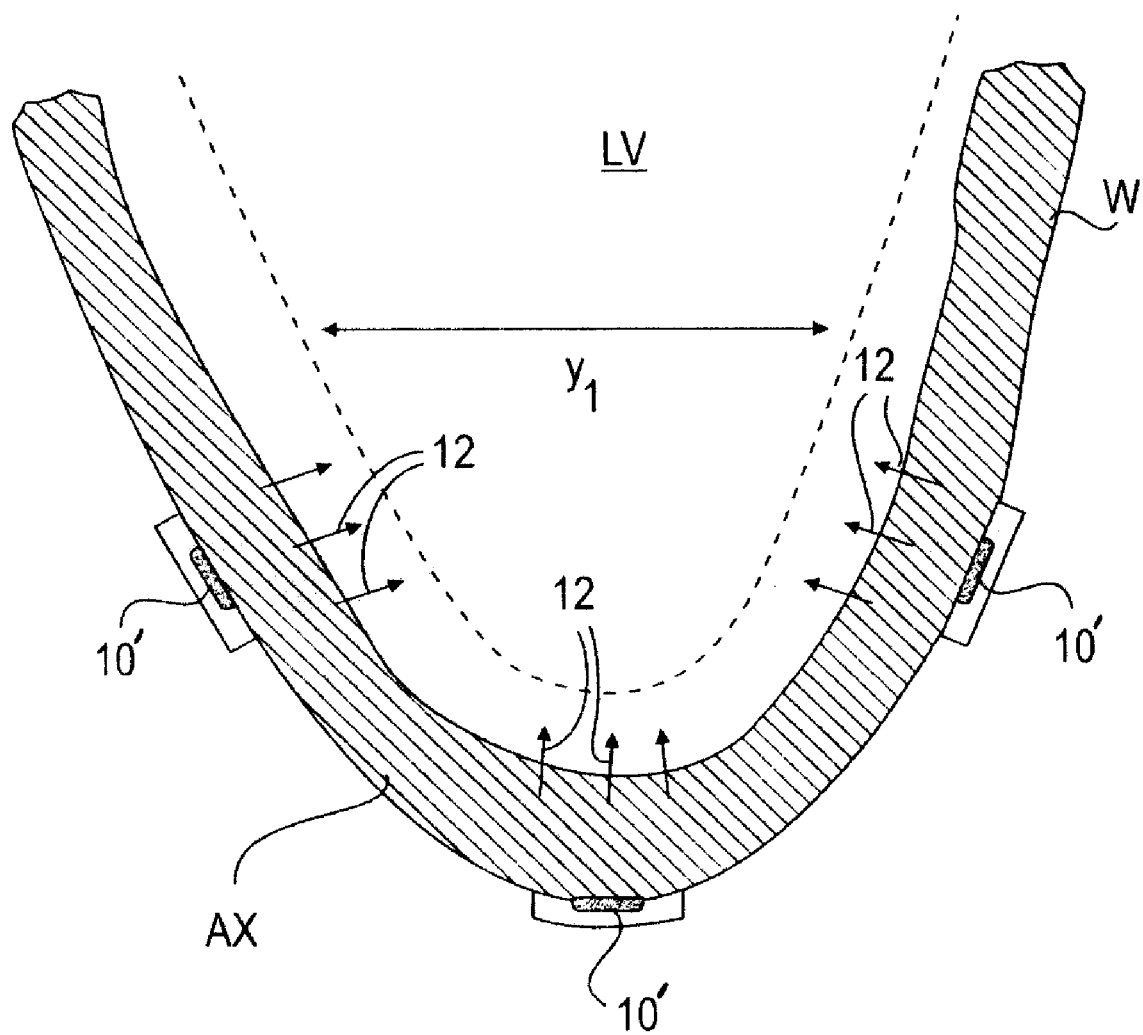
FIG. 10 illustrates magnetic elements implanted on an external surface of the left ventricle according to one embodiment.

Alternatively or in addition, magnetic elements 10' may be positioned on an external surface of the heart. In preferred embodiments, the magnetic elements 10' are positioned on the external surfaces of the walls of the ventricles. For example, as illustrated in FIG. 10, magnetic elements 10' may be implanted on the surface of the left ventricle LV near the apex AX of the heart. The magnetic elements 10' have opposing poles so that the magnetic elements 10' attract each other, as indicated by arrows 12. Such attraction draws the walls W of the left ventricle LV inward, toward each other, thereby reshaping the left ventricle LV. The width of the left ventricle LV is thus reduced toward normal width $y_1$. The magnetic forces are able to assist the left ventricle LV throughout the cardiac cycle, increasing the contractibility of the left ventricle LV. This increases the stroke volume (SV) which increases the cardiac output (CO).

Externally placed magnetic elements 10' may have any of the forms described and illustrated above and may optionally include a patch to assist in attaching the magnetic element 10' to the heart wall W. FIGS. 11A-11B illustrate an embodiment of a magnetic element 10' including a magnetic core 70 attached to a patch 72. In this embodiment, the core 70 is in the shape of a disc having a diameter in the range of approximately 0.1-3 mm and a thickness of 0.1-3 mm. It may be appreciated that the magnetic core 70 may have any suitable size and shape, including discs, cones, rods, blocks, spheres, and rings to name a few. The magnetic core 70 is comprised of any suitable magnetic material, such as Neudynium Iron Boron (Nd Fe B), Samarium Cobalt (Sm Co) or Aluminum Nickel Cobalt (Al Ni Co). Such a magnetic core 70 can provide a static magnetic field of approximately 300 Gauss.

In this embodiment illustrated in FIG. 11A, the magnetic core 70 is disposed in the center of the patch 72. The patch 72 may be comprised of any material which provides suitable flexibility and mating with the surface of the heart, such as Dacron®. In this embodiment, the patch 72 has a circular shape with a diameter in the range of approximately 0.120-0.500 inches and a thickness in the range of approximately 0.005-0.050 inches. The patch 72 may also include suture holes 74 to assist in suturing the patch to the heart wall. In preferred embodiments, the patch 72 includes 6-12 suture holes 74 located around the peripheral edge of the patch 72. Each suture hole 74 may have a diameter of 0.010±0.005 inches. FIG. 11B provides a cross-sectional view of the magnetic element 10' of FIG. 11A.

FIGS. 12A-12B illustrate a similar embodiment wherein the magnetic element 10' includes two magnetic cores 70a, 70b disposed on the patch 72. Here, the magnetic cores 70a, 70b have opposite charges. It may be appreciated that any number of magnetic cores may be disposed on the patch 72, and the magnetic cores may have any charge and may be in any arrangement.

FIGS. 13A-13B illustrate another embodiment of a magnetic element 10' including a magnetic core 80 attached to a patch 82. In this embodiment, the core 80 is in the shape of a disc having a diameter in the range of approximately 0.040-0.120 inches and a thickness of 0.010-0.120 inches. It may be appreciated that the magnetic core 80 may have any suitable size and shape, including discs, cones, rods, blocks, spheres, and rings to name a few. The magnetic core 80 is comprised of any suitable magnetic material, such as Neudynium Iron Boron (Nd Fe B), Samarium Cobalt (Sm Co) or Aluminum Nickel Cobalt (Al Ni Co).

In this embodiment illustrated in FIG. 13A, the magnetic core 80 is disposed in the center of the patch 82. The patch 82 may be comprised of any material which provides suitable flexibility and mating with the surface of the heart, such as Dacron®. In this embodiment, the patch 82 has a circular shape with a diameter in the range of approximately 0.120-0.500 inches and a thickness of approximately 0.040±0.005 inches. FIG. 13B provides a cross-sectional view of the magnetic element 10' of FIG. 13A.

The magnetic elements 10' are attached to the external surface of the heart by open heart surgical methods or minimally invasive thoracoscopic methods. The patches are typically sewn to the heart with the use of sutures. Alternatively or in addition, the patches may be glued to the heart with a tissue adhesive. As mentioned above, the magnetic forces are able to assist the ventricles throughout the cardiac cycle, increasing the contractibility of the ventricles. This increases the stroke volume (SV) which increases the cardiac output (CO).

Figure 14A:
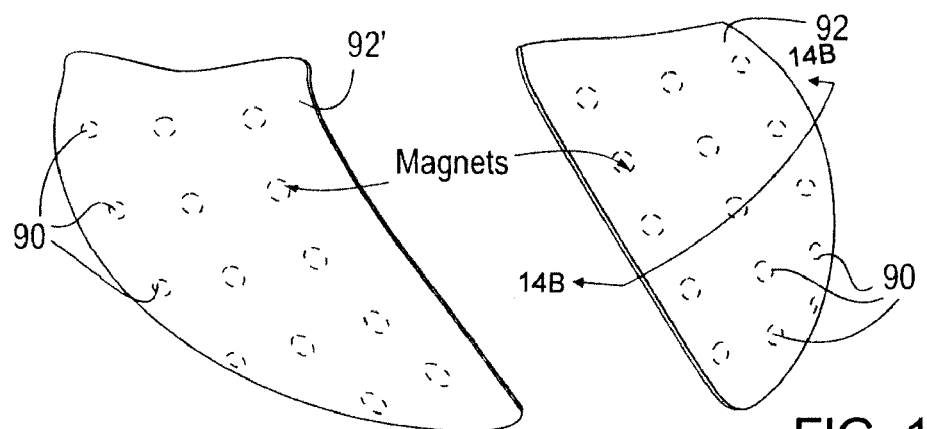
FIGS. 14A-14C illustrate an embodiment of a magnetic element which includes a plurality of magnetic cores disposed on a larger patch.
Figure 14B:
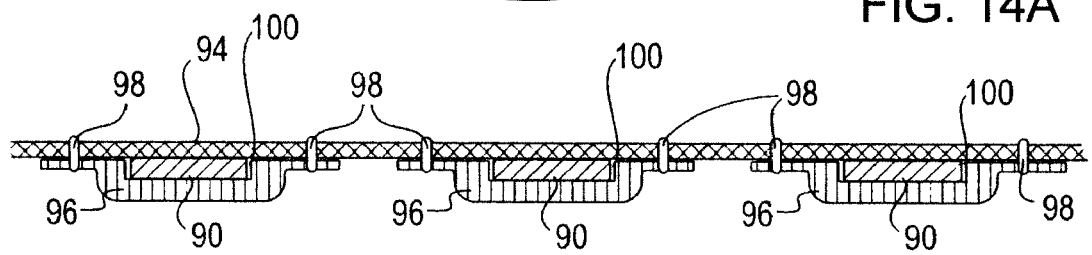
Figure 14C:
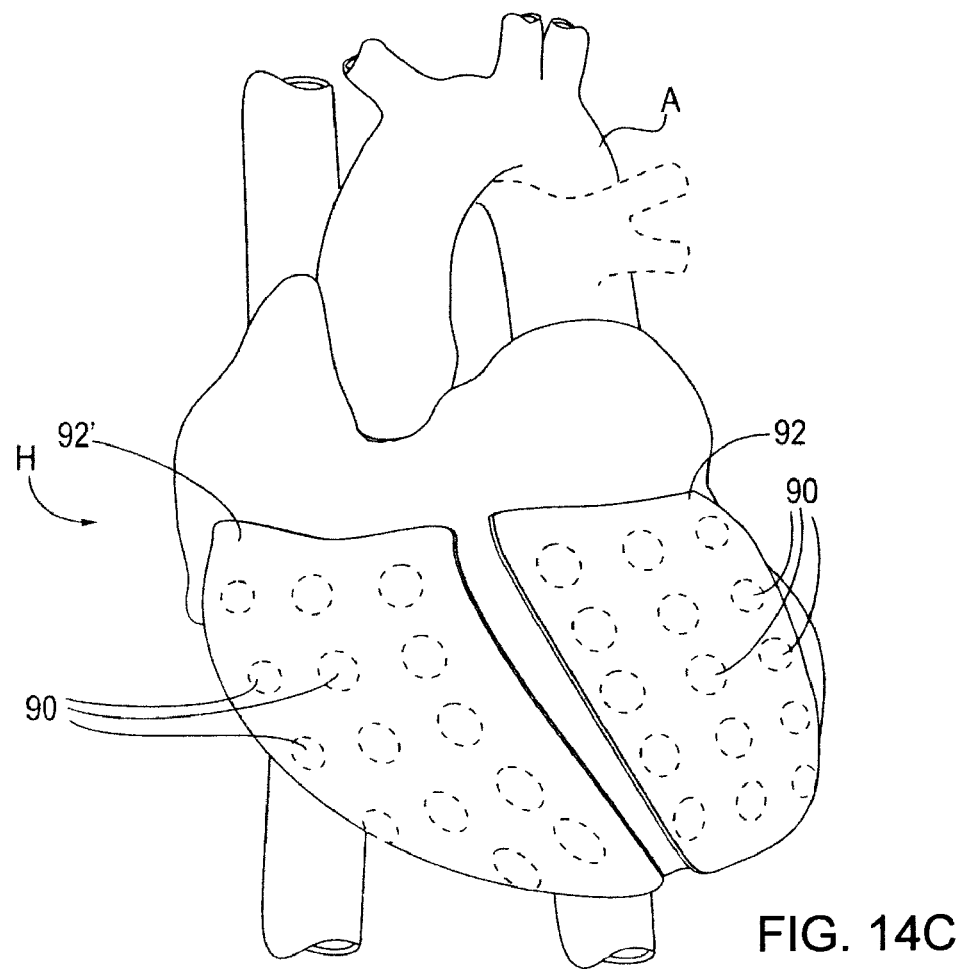

FIGS. 14A-14C illustrate yet another similar embodiment wherein the magnetic element 10' includes a plurality of magnetic cores 90 disposed on a larger patch 92. In this embodiment, the cores 90 are in the shape of individual discs having diameters in the range of approximately 0.040-0.120 inches and thicknesses of 0.010-0.120 inches. It may be appreciated that the magnetic cores 90 may have any suitable size and shape, including discs, cones, rods, blocks, spheres, and rings to name a few. The magnetic cores 90 are comprised of any suitable magnetic material, such as Neudynium Iron Boron (Nd Fe B), Samarium Cobalt (Sm Co) or Aluminum Nickel Cobalt (Al Ni Co). The larger patch 92 may be comprised of any material which provides suitable flexibility and mating with the surface of the heart, such as Dacron®.

The larger patch 92 is sized and shaped to cover a more extensive portion of the surface of the heart, such as a surface covering an atrium or ventricle. FIG. 14A illustrates two such patches 92, 92', a left ventricle patch 92 and a right ventricle patch 92'. It may be appreciated that any number of magnetic cores 90 may be disposed on the patches 92, 92', and the magnetic cores 90 may have any charge and may be in any arrangement. The cores 90 may also be attached to the patches 92, 92' by any suitable means, such as by suturing, adhering with adhesive, or confining in a pocket. FIG. 14B illustrates a cross-sectional view of the patch 92. As shown, the patch 92 is comprised of a first layer of material 94 and a second layer of material 96, wherein the magnetic cores 90 are captured between the layers 94, 96. The layers 94, 96 may be sutured 98 or sewn together creating pockets 100 within which the cores 90 reside.

The magnetic elements 10' are attached to the external surface of the heart, as illustrated in FIG. 14C, by open heart surgical methods or minimally invasive thoracoscopic methods. The patches 92, 92' are typically sewn to the heart with the use of sutures. Alternatively or in addition, the patches 92, 92' may be glued to the heart with a tissue adhesive. In some embodiments, the cores 90 on the left ventricle patch 92 are positively charged and the cores on the right ventricle patch 92' are negatively charged. Thus, the oppositely charged patches 92, 92' apply force to opposite sides of the heart, compressing the ventricles therebetween. The magnetic forces are able to assist the ventricles throughout the cardiac cycle, increasing the contractibility of the ventricles. This increases the stroke volume (SV) which increases the cardiac output (CO).

Figure 15A:
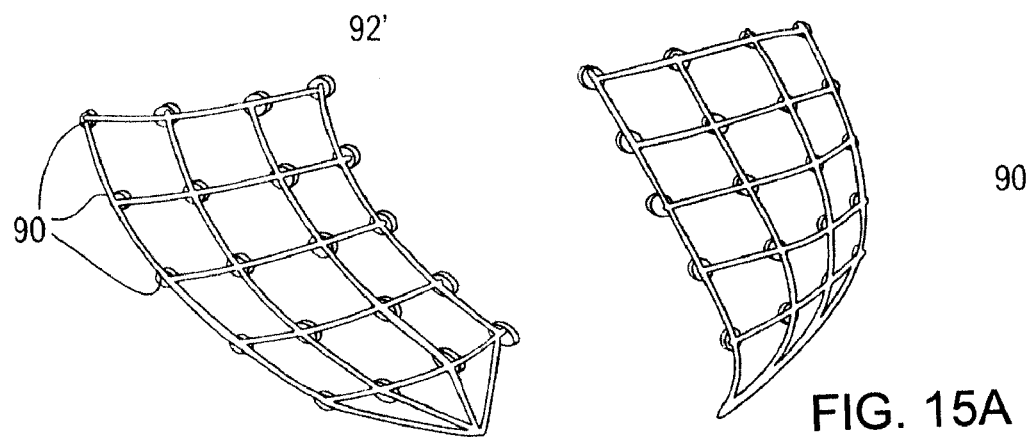
FIGS. 15A-15B illustrate an embodiment of a magnetic element wherein each of the patches are comprised of a net.
Figure 15B:
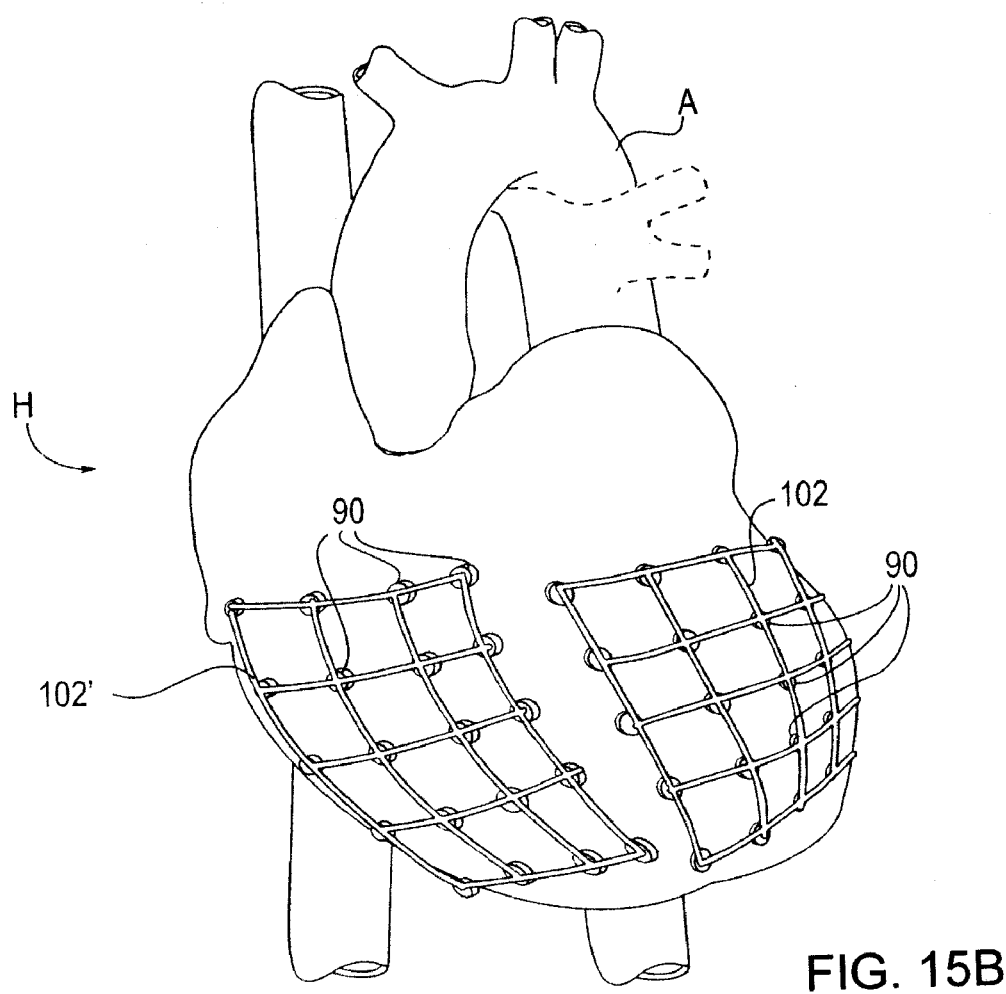

FIGS. 15A-15B illustrate another embodiment wherein each of the patches are comprised of a net 102, 102' respectively. The nets 102, 102' have the form of an openwork mesh made of strands that are woven or knotted together at regular or irregular intervals. The strands may be comprised of suture, threads, filaments, wires or other suitable materials and may be elastic or non-elastic. The magnetic cores 90 typically have the same features as described above. The cores 90 may also be attached to the nets 102, 102' by any suitable means, such as by suturing or adhering with adhesive. The cores 90 may be attached at any locations and in any arrangement on the nets 102, 102'. The nets 102, 102' are sized and shaped to cover a desired portion of the surface of the heart, such as a surface covering an atrium or ventricle.

The magnetic elements 10' are attached to the external surface of the heart, as illustrated in FIG. 15B, by open heart surgical methods or minimally invasive thoracoscopic methods. The nets 102, 102' are typically sewn to the heart with the use of sutures and/or glued to the heart with a tissue adhesive. Again, in some embodiments, the cores 90 on a left ventricle net 102 are positively charged and the cores on the right ventricle net 102' are negatively charged. Thus, the oppositely charged nets 102, 102' apply force to opposite sides of the heart, compressing the ventricles therebetween. The magnetic forces are able to assist the ventricles throughout the cardiac cycle, increasing the contractibility of the ventricles. This increases the stroke volume (SV) which increases the cardiac output (CO).

C. Shape Memory Reinforcement Elements

In another embodiment, the reinforcement elements 10 include shape memory material and the geometry of the ventricles is changed by placing the shape memory reinforcement elements 10 (referred to herein as shape memory elements 10") on or within tissue areas or walls of the ventricles. A variety of shape-memory materials may be used and will be described in detail hereinbelow. In general, however, shape memory is the ability of a material to revert to at least one shape held in its memory when actuated by an environmental change. Examples of such environmental changes include changes in temperature, application of light, changes in ionic concentration and/or pH, or application of an electric field, magnetic field or ultrasound, to name a few. In some embodiments, the material can also typically resume its original shape by return of the environmental condition, thus having a two-way effect.

Figure 16A:
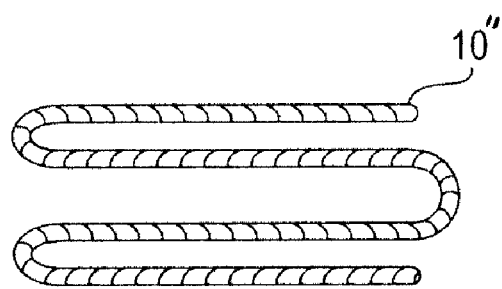
FIGS. 16A-16B illustrate a shape memory element holding an original compressed folded shape and a memory expanded folded shape according to one embodiment.
Figure 16B:
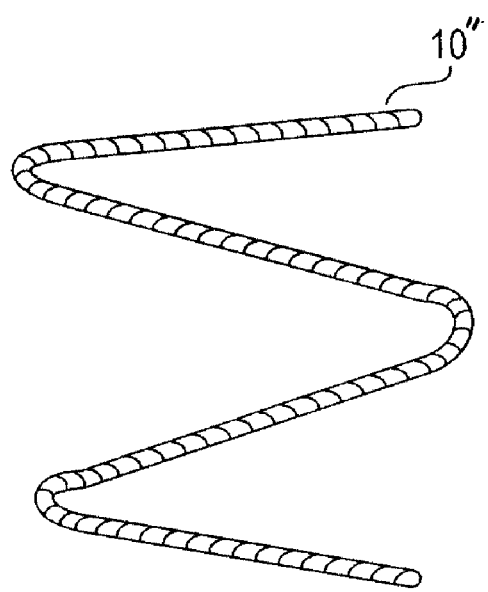

FIGS. 16A-16B illustrate a shape memory element 10" holding two different shapes, an original shape (FIG. 16A) and a memory shape (FIG. 16B). The shape memory element 10" has the original shape in a common environment, in this instance a compressed folded shape, and maintains the memory shape, in this instance an expanded folded shape, in its memory. The shape memory element 10" can be used in a variety of manners while in the original shape, in anticipation of reverting the shape memory element 10" to its memory shape at a future time. Optionally, the shape memory element 10" could additionally be reverted back to its original shape at yet another future time.

Figure 17A:
FIGS. 17A-17B illustrate a shape memory element holding an original straight shape and a memory folded shape according to one embodiment.
Figure 17B:
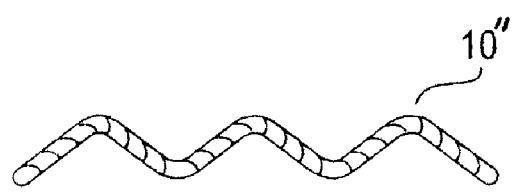

Similarly, FIGS. 17A-17B illustrate a shape memory element 10" holding two different shapes, an original shape (FIG. 17A) and a memory shape (FIG. 17B). The shape memory element 10" has the original shape in the common environment, in this instance a straight shape, and maintains the memory shape, in this instance a folded shape, in its memory. The shape memory element 10" may have the form of a rod or ribbon structure, and, in some embodiments, have a diameter in the range of approximately 0.25-0.5 mm and a thickness in the range of approximately 0.05-0.1 mm. Referring to FIG. 18A, the shape memory elements 10" in their original straight shape may be implanted within the walls W of the right ventricle RV and left ventricle LV near the apex AX of the heart H. As shown, the ventricles RV, LV are expanded and have widths $x_2$ and $y_2$ respectively. The shape memory elements 10" may then be reverted to their memory folded shape, FIG. 18B, by application of an environmental factor, such as a temperature change, a magnetic field, etc. Upon application, the shape memory elements 10" begin to fold and retract, drawing the tissue of the ventricle walls together in a contracted fashion. This in turn reshapes the ventricles RV, LV toward their normal width $x_1$ and width $y_1$, respectively. The shape changes of the ventricles RV, LV increase the contractibility of the ventricles RV, LV. This increases the stroke volume (SV) which increases the cardiac output (CO).

Figure 19A:
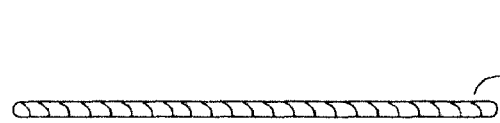
FIGS. 19A-19B illustrate a shape memory element holding an original straight shape and a memory curved shape according to one embodiment.
Figure 19B:
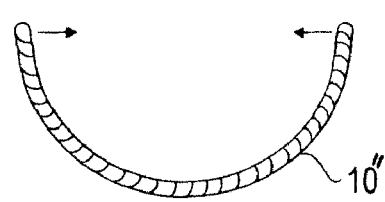
Figure 19C:
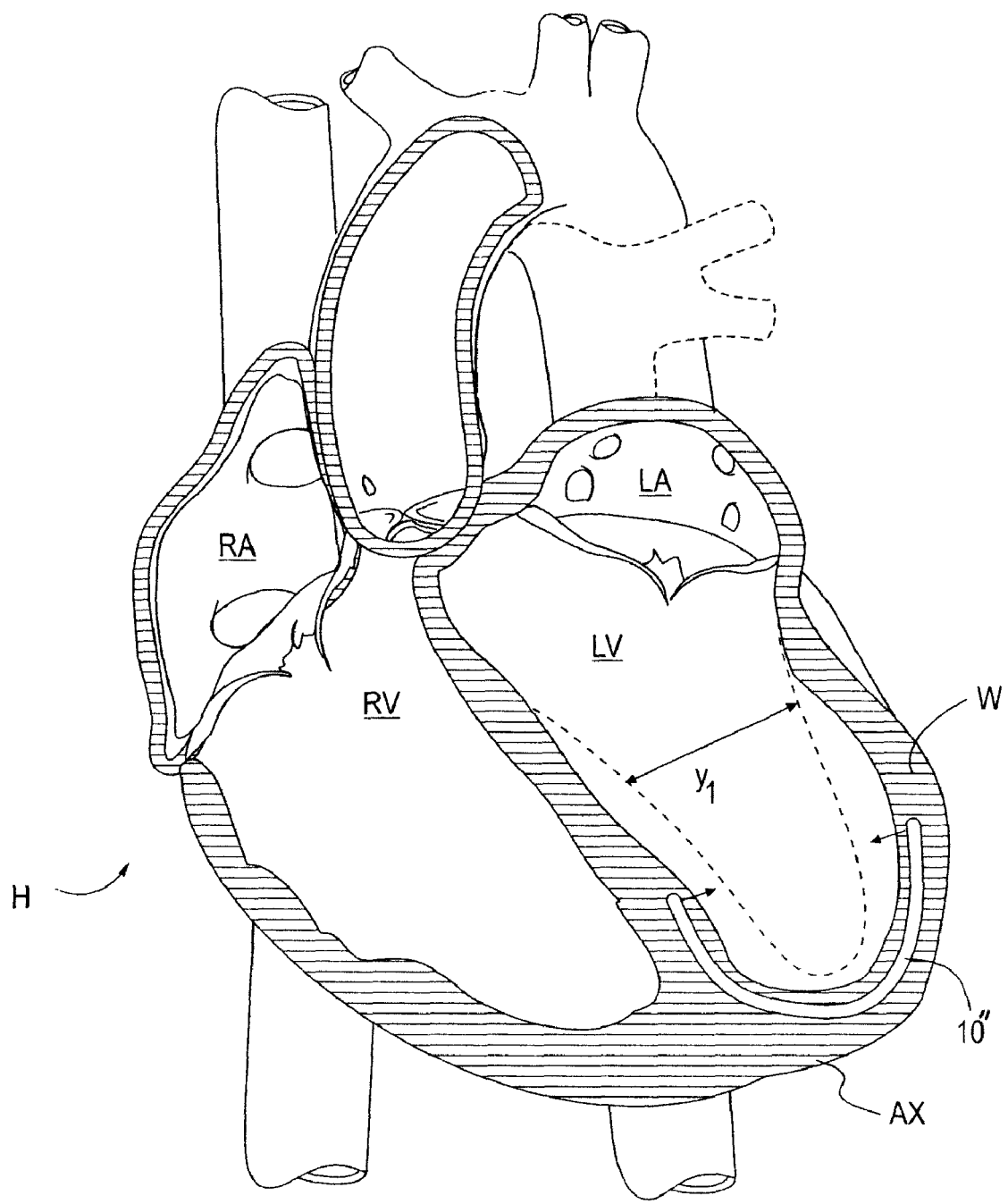
FIG. 19C illustrates the shape memory element of FIGS. 19A-19B implanted within the walls of the heart according to one embodiment.

Further, FIGS. 19A-19B illustrate a shape memory element 10" holding two different shapes, an original shape (FIG. 19A) and a memory shape (FIG. 19B). The shape memory element 10" has the original shape in the common environment, in this instance a straight shape, and maintains the memory shape, in this instance a curved shape, in its memory. Referring to FIG. 19C, a shape memory element 10" in its original straight shape may be implanted within the walls W of a ventricle, such as the left ventricle LV as shown. Due to its positioning along the apex AX of the heart H, the shape memory element 10" takes on a slight curvature. The shape memory element 10" may then be reverted to its memory curved shape of FIG. 19B by application of an environmental factor, such as a temperature change, a magnetic field, etc. Upon application, the shape memory element 10" begins to curve inwardly as indicated by arrows. Such curving draws the walls W of the left ventricle LV inward, toward each other, thereby reshaping the left ventricle LV. The width of the left ventricle LV is thus reduced toward the normal width $y_1$. The shape change of the ventricle LV increases the contractibility of the ventricle LV. This increases the stroke volume (SV) which increases the cardiac output (CO).

It may be appreciated that the implanted shape memory elements 10" may vary by original shape, memory shape, length, width, size, material, environmental actuation factor, and rate or extent of change, to name a few. Further, the shape memory elements 10" may be actuated at the same or varied times. Likewise, in some embodiments, the shape memory elements 10" may remain in their memory shape or be reverted toward their original shape at any time, and at the same or varied times. This may be repeated any number of times.

It may also be appreciated that any number of shape memory elements 10" may be used and that the shape memory elements 10" may be positioned at any location on (externally or internally) or within the walls W of the heart H, including the right atrium RA, right ventricle RV, left atrium LA and left ventricle LV, which includes the septal wall. It may further be appreciated the shape memory elements 10" may be positioned on or within the valves, including the mitral valve MV, aortic valve AV, tricuspid valve TV, and pulmonary valve (not shown), and/or any of the associated anatomy, such as the aorta A, pulmonary artery, pulmonary vein, chordae etc. Further, the shape memory elements 10" may be positioned at one area to change the shape of a different area. For example, shape memory elements 10" may be positioned within the left atrium LA to change the shape of the mitral valve MV. In some embodiments, one or more shape memory elements 10" are positioned within the coronary sinus to change the shape of the mitral valve annulus. The coronary sinus is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. One or more shape memory elements 10" may be introduced into the coronary sinus and then activated to change shape which in turn reshapes and advantageously effects the geometry of the mitral valve annulus.

Figure 20A:
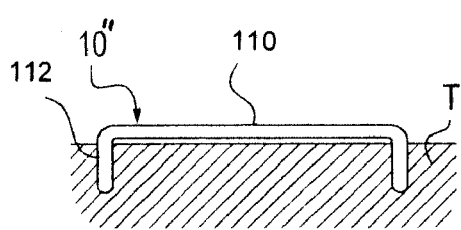
FIGS. 20A-20B illustrate a shape memory element having a staple-like original shape according to one embodiment.
Figure 20B:
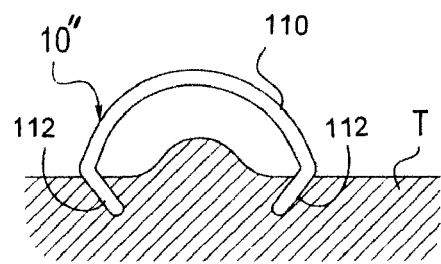

It may also be appreciated that the shape memory elements 10" may be fully implanted, partially implanted or otherwise attached to the tissues of the heart. For example, as shown in FIG. 20A, a shape memory element 10" may have a staple-like original shape having two prongs 112 which are penetratable into tissue T and are connected by a straight portion 110 which resides above or on the surface of the tissue T. Upon activation, the shape memory element 10" changes to its memory shape, as shown in FIG. 20B. Here, the straight portion 110 bends or curves, directing the prongs 112 toward each other along with the associated tissue T. Such a shape memory element 10" may be used on any surface (external or internal) of the heart or related anatomy to plicate or otherwise draw tissue together. It may be appreciated that the shapes may be reversed, i.e. the original shape being the curved shape of FIG. 20B and the memory shape being the staple-like shape of FIG. 20A. In such instance, the shape memory element 10" may be used to extend tissue segments.

Figure 21A:
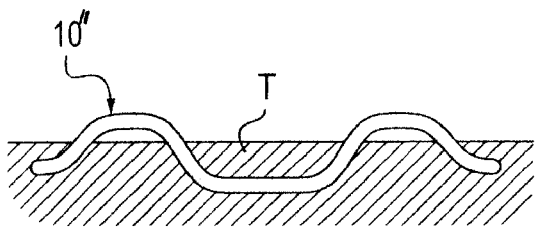
FIG. 21A-21B illustrate a shape memory element having a suture-like shape which can be stitched into the tissue according to one embodiment.
Figure 21B:
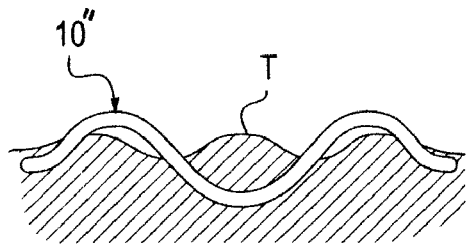

Similarly, as shown in FIG. 21A, a shape memory element 10" may have an elongate shape which is "stitched" through tissue T. Thus, portions of the shape memory element 10" lay above or on the surface of the tissue T and portions lay within the tissue T. Upon activation, the shape memory element 10" changes to its memory shape, as shown in FIG. 21B. Here, the shape memory element 10" contracts along with the associated tissue T. Such a shape memory element 10" may be used on any surface (external or internal) of the heart or related anatomy to plicate or otherwise draw tissue together. It may be appreciated that the shapes may be reversed, i.e. the original shape being the contracted shape of FIG. 21B and the memory shape being the extended shape of FIG. 21A. In such instance, the shape memory element 10" may be used to extend tissue segments.

Figure 22A:
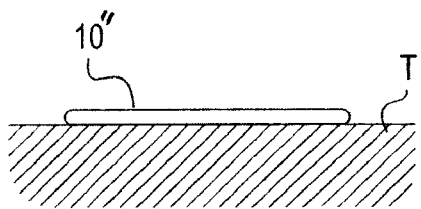
FIGS. 22A-22C illustrate shape memory elements attached to the surface of tissue according to one embodiment.
Figure 22B:
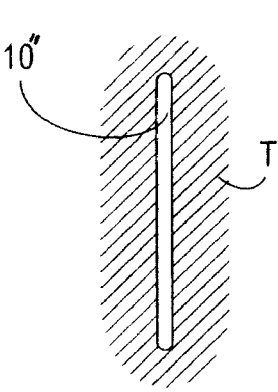
Figure 22C:
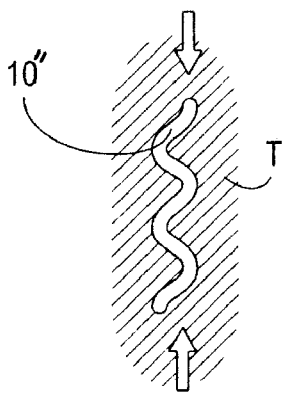

FIGS. 22A-22C illustrate shape memory elements 10" attached to the surface of tissue T. FIG. 22A provides a side view of a shape memory element 10" having a straight original shape wherein the shape memory element 10" is attached to the tissue T by any suitable mechanism or methods, such as by adhesive or suturing. FIG. 22B provides a top view of the shape memory element 10" of FIG. 22A. Upon activation, the shape memory element 10" changes to its memory shape, as shown in FIG. 22C. Here, the shape memory element 10" bends, curves or folds, contracting the associated tissue T. Such a shape memory element 10" may be used on any surface (external or internal) of the heart or related anatomy to plicate or otherwise draw tissue together. It may be appreciated that the shapes may be reversed, i.e. the original shape being the curved shape of FIG. 22C and the memory shape being the straight shape of FIGS. 22A-22B. In such instance, the shape memory element 10" may be used to extend tissue segments.

1. Types of Shape Memory Materials

As mentioned, a variety of shape memory materials may be used. The following types of materials are provided by way of illustration and example and should not be taken as limiting in scope of the disclosed embodiments.

(a). Temperature Activated Shape Memory Metals

The shape memory elements 10" may be comprised of shape memory metal alloys (SMAs), including Ni—Ti (Nitinol®), Cu—Zn—Al, Cu—Al—Ni and Fe—Ni—Al alloys. SMAs undergo changes in crystal structure at certain temperatures called transformation temperatures. Typically, SMAs exist in two different temperature-dependent crystal structures (phases) called martensite (lower temperature) and austenite (higher temperature or parent phase). The crystal structure of the austenite phase has a higher symmetry than the martensite phase. For example, for Cu—Al—Ni, the structure changes from cubic to orthorhombic. When a martensite SMA is heated, it begins to change into austenite. The temperature at which this phenomenon starts is called austenite start temperature (As). The temperature at which this phenomenon is complete is called austenite finish temperature (Af). When the austenite SMA is cooled, it begins to change onto martensite. The temperature at which this phenomenon starts is called martensite start temperature (Ms). The temperature at which martensite is again completely reverted is called martensite finish temperature (Mf). In addition, a rhombohedral phase is produced during cooling from the high temperature austenite phase to the low temperature martensite phase. The temperature at which this phenomenon starts is called rhombohedral start temperature (Rs) and the temperature at which this phase is completed is called rhombohedral finish temperature (Rf). Typical temperature ranges for these phases are as follows:

| | |
|---|---|
| Austenite | As = 42° C.~53° C. |
| | Af = 45° C.~70° C. |
| Rhombohedral | Rs = 30° C.~50° C. |
| | Rf = 20° C.~35° C. |
| Martensite | Ms = 10° C.~20° C. |
| | Mf = −1° C.~15° C. |

However, it may be appreciated that composition and metallurgical treatments have dramatic impacts on the above transition temperatures. In any case, the low temperature martensite structure of the SMA allows the SMA to be easily and seemingly permanently deformed. However on heating, the SMA returns to its high temperature austenite structure which is of the memory shape. Thus the material has "remembered" its shape.

Thus, a shape memory element 10" comprised of an SMA may be implanted within, partially within or attached to tissue of the heart H when in its original shape. Energy or heat is then applied to the shape memory element 10" to raise the temperature of the shape memory element 10" above its transformation temperature, such as to a temperature in the range of approximately 37° C.-70° C. This causes the shape memory element 10" to change shape to its memory shape which reconfigures the tissue. If desired, at any time, the shape memory element 10" may be cooled to below its transformation temperature to change the shape memory element 10" back to its original shape.

(b). Ferromagnetic Shape Memory Metals

The shape memory elements 10" may be comprised of magnetically controlled shape memory material (MSMs), including Fe—C, Fe—Pd, Fe—Mn—Si, Co—Mn, Fe—Co—Ni—Ti, Ni2MnGa, Co—Ni—Al, Ni—Mn—Ga, to name a few. MSMs exhibit a paramagnetic/ferromagnetic transition besides a thermoelastic martensitic transformation. Generally, MSM material consists of internal areas, twin variants. These variants have different magnetic and crystallographic orientations. When the MSM material is subjected to a magnetic field the proportions of the variants change resulting in a shape change of the element. MSM material can be made to change shape in a variety of different ways, such as to elongate axially, bend or twist.

A shape memory element 10" comprised of an MSM may be implanted within, partially within or attached to tissue of the heart H when in its original shape. A magnetic field is then applied to the shape memory element 10" which causes the element to change shape. The magnetic field can be applied with, for example, the use of a clinically available magnetic resonance imaging (MRI) machine. Such change of shape reconfigures the associated tissue. If desired, at any time, the shape memory element 10" may be changed back to its original shape by reapplication of a magnetic field. And, since shape memory elements 10" comprised of MSMs rely on magnetic fields rather than temperature changes to change shape, the risk of overheating healthy tissue is minimized.

Examples of suitable MSMs are provided in Tellinen, J. et al. "Basic Properties of Magnetic Shape Memory Actuators," published in 8th international conference ACTUATOR 2002, Bremen, Germany, 10-12 Jun. 2002; Oikawa, et al. "Development of Co—Ni—Al-based Ferromagnetic Shape Memory Alloys," AIST Today; Vol. 1, No. 7 (2001) 20; and Cohen-Kami et al. "Fe—Pd Alloy Ferromagnetic Shape Memory Thin Films," Technion-Israel Institute of Technology in collaboration with Dr. Joost J. Vlassak and Dr. Yuki Sugimura of Harvard University, Research Experience for Undergraduates (REU), 2003, all of which are incorporated herein by reference for all purposes.

(c). Shape Memory Polymers

The shape memory elements 10" may be comprised of shape memory polymers (SMPs). Such SMPs may hold one shape in memory or may hold more than one shape in memory.

SMPs which hold one shape in memory are generally characterized as phase segregated linear block co-polymers having a hard segment and a soft segment. The hard segment is typically crystalline, with a defined melting point, and the soft segment is typically amorphous, with a defined glass transition temperature. Sometimes, however, the hard segment is amorphous and the soft segment is crystalline. In any case, the melting point or glass transition temperature of the soft segment is substantially less than the melting point or glass transition temperature of the hard segment. Changes in temperature cause the SMP to revert between the original shape and the memory shape.

Examples of polymers used to prepare hard and soft segments of SMPs include various polyethers, polyacrylates, polyamides, polysiloxanes, polyurethanes, polyether amides, polyurethane/ureas, polyether esters, and urethane/butadiene copolymers. For example, see U.S. Pat. Nos. 5,506,300; 5,145,935; 5,665,822, incorporated herein by reference for all purposes.

SMPs which hold more than one shape in memory may include, for example, a hard segment and at least two soft segments. The transition temperature of the hard segment is at least 10° C., and preferably 20° C., higher than the transition temperature of one of the soft segments, and the transition temperature of each subsequent soft segment is at least 10° C. and preferably 20° C. lower than the transition temperature of the preceding soft segment. Thus, an element formed from such an SMP will change shape as the temperature moves through the transition temperatures. Examples of such SMPs are described in U.S. Pat. Nos. 6,720,402 and 6,388,043, and in Lendlein, A et al. "Biodegradable, Elastic Shape-Memory Polymers for Potential Biomedical Applications", SCIENCE Vol. 296, 31 May 2002, all of which are incorporated herein by reference for all purposes. In addition, examples of such SMPs include Calo-MER™, a shape memory thermoplastic provided by The Polymer Technology Group (Berkeley, Calif.), and various shape memory polymers provided by mnemoScience GmbH (Pauwelsstraβe 19, D-52074 Aachen, and Institute for Technical and Macromolecular Chemistry, RWTH Aachen, Germany).

It may be appreciated that although these SMPs are described as changing shape in response to change in temperature, in some embodiments, the SMPs change shape in response to application of light, changes in ionic concentration and/or pH, electric field, magnetic field or ultrasound, to name a few. For example, an SMP can include at least one hard segment and at least one soft segment, wherein at least two of the segments, preferably two soft segments, are linked to each other via a functional group that is cleavable under application of light, electric field, magnetic field or ultrasound. The temporary shape is fixed by crosslinking the linear polymers. By cleaving those links the original shape can be recovered. The stimuli for crosslinking and cleaving these bonds can be the same or different.

Figure 23:
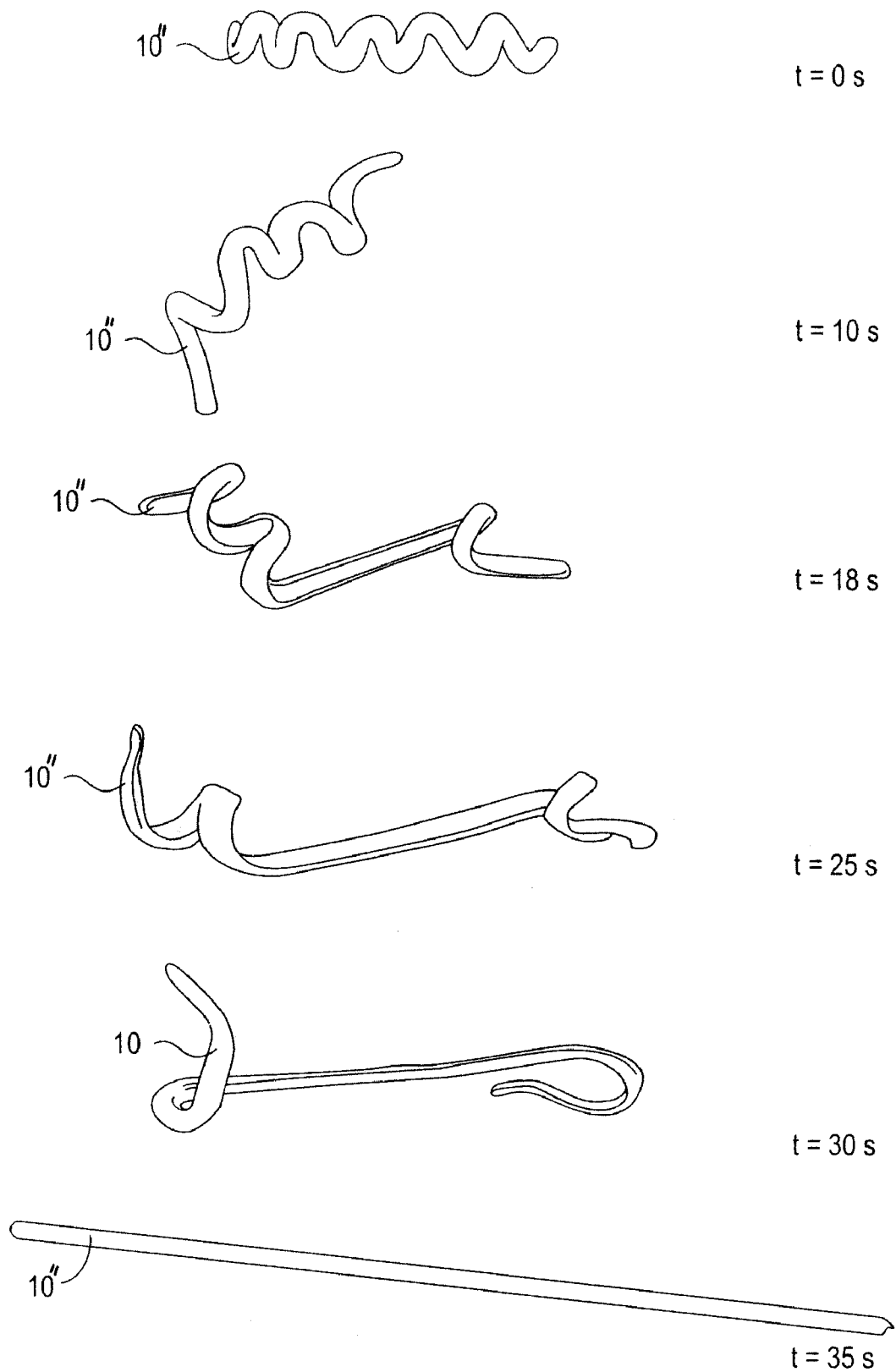
FIG. 23 illustrates a shape memory polymer transitioning between shapes according to one embodiment.

In some instances, shape memory polymers are preferred over metallic shape memory alloys due to limitations associated with metallic shape memory alloys, such as time consuming manufacturing processes, higher manufacturing cost, high temperature treatment and limited deformation (up to 8%). Many of these limitations are resolved by using shape memory polymers. Shape memory polymers can be easily manufactured at a very low cost. In addition, the transition temperature may be easily adjusted, wherein such adjustment is more difficult with metals. Further, the polymers may be programmed into shape in seconds at about 60-70° C. and can withstand deformations of several hundred percent. In some embodiments, the entire transition occurs within 35 seconds, as illustrated in FIG. 23 which depicts the uncoiling of an SMP provided by mnemoScience GmbH.

It may be appreciated that in some embodiments the shape memory elements are biodegradable. Examples of degradable polymeric shape memory materials include poly lactic acid (PLA), poly glycolic acid (PLGA). PLA and PLGA are hydrophobic and absorbed slowly in vivo. Therefore, after 6-12 months (for example) of implantation, the heart tissue may be reshaped and the shape memory elements may be partially or completely absorbed into the body. It may also be appreciated that some metallic shape memory materials may also be biodegradable.

2. Shape Memory Coatings

In addition to the coatings or coverings discussed above, or in other embodiments, the shape memory elements 10" disclosed herein may include other coatings or coverings that may be present in any number and in any combination.

In some embodiments, the shape memory elements 10" are covered with a magnetic resonance imaging (MRI) absorbing coating. Such a coating may allow more focused and rapid heating of a shape memory element 10" while minimizing heat absorption by surrounding tissue. An example of such a coating is provided by Biophan Technologies, Inc. of West Henrietta, N.Y.

Similarly, in some embodiments, the shape memory elements 10" are covered with a high, medium or low intensity focused ultrasound absorbing coating or hydrogel material. Ultrasound therapy employs ultrasound transducers that are capable of delivering 1-500 W/cm$^2$, or more preferably 2-50 W/cm$^2$, at a frequency in the range of 0.5-30 MHz, to a focal spot. A portion of the energy from these high intensity sound waves is transferred to the targeted location as thermal energy. Thus, such a coating will allow more focused and rapid heating of a shape memory element 10" while minimizing heat absorption by surrounding tissue. Examples of such coatings are provided by U.S. Patent Publication No. 2003/0233045 A1 and 2004/0234453 A1, incorporated herein by reference for all purposes.

Figure 24:
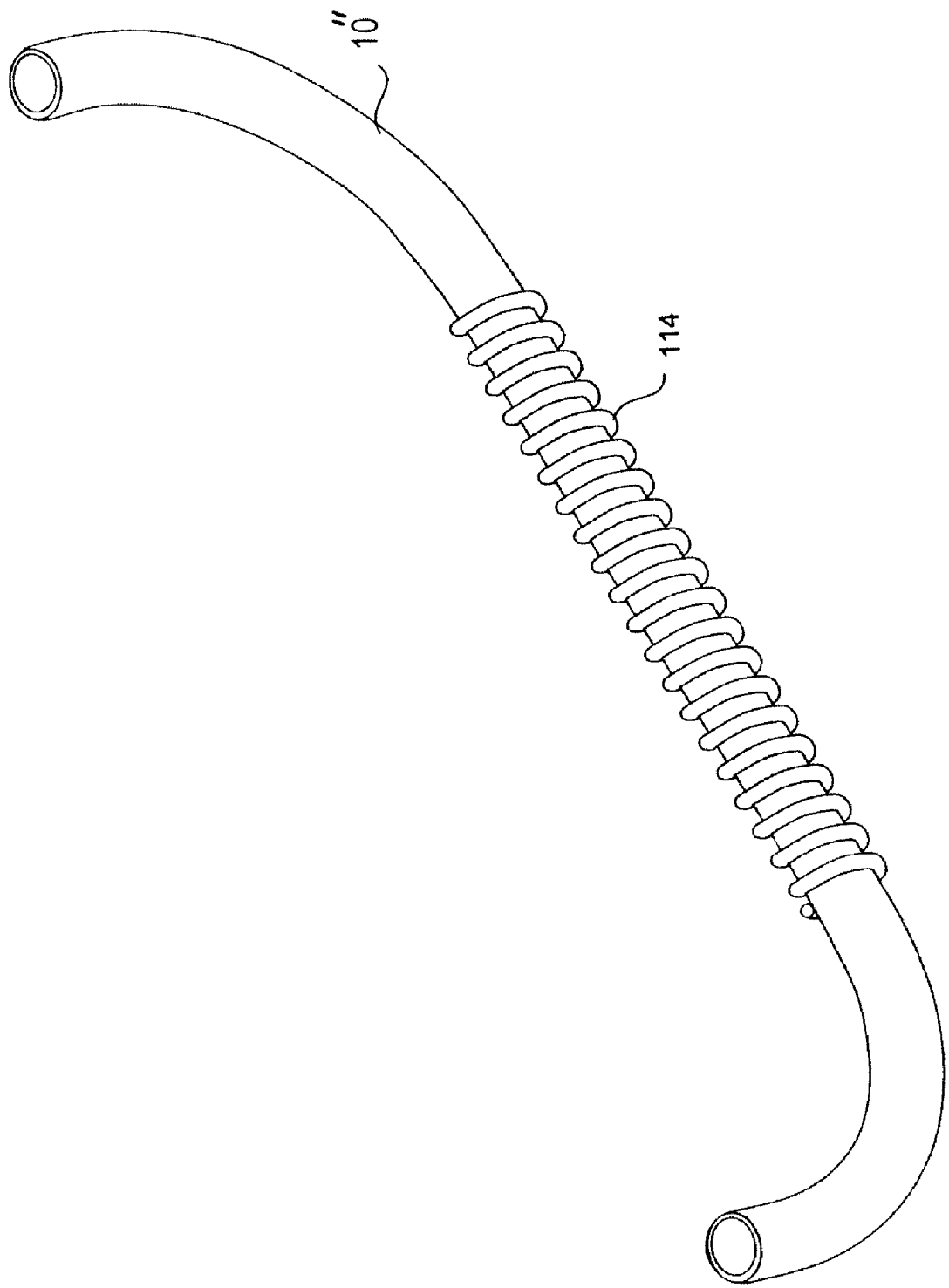
FIG. 24 illustrates an embodiment of a conductive wire wrapped around a shape memory element according to one embodiment.

In some embodiments, the shape memory elements 10" are covered with one or more fine conductive wires 114, as illustrated in FIG. 24 The wires 114 are wrapped around the shape memory elements 10" in any suitable configuration. FIG. 24 illustrates a single conductive wire 114 wrapped around the shape memory element 10" forming a coil shape. The one ore more wires 114 may be comprised of any suitable conductive material, such as platinum coated copper, titanium, tantalum, stainless steel or gold, to name a few. The presence of the wires allow more focused and rapid heating of the shape memory element 10" while minimizing undesired heating of surrounding tissues.

In some embodiments, the shape memory elements 10" are comprised of layers of various materials. For example, a shape memory element 10" may be comprised of a non-shape memory material (such as a metal, metal alloy or plastic) core with an outer coating of shape memory material (such as a SMA, MSM or SMP), or vice versa. Or, a shape memory element 10" may be comprised of a shape memory core with a biocompatible polymer coating. In one embodiment, the core comprises a Nitinol® rod having a length of approximately 20-40 mm and a diameter of approximately 0.25-0.5 mm. The core is coated with a thin layer of biocompatible polymer, approximately 0.1-0.3 mm thick. Examples of biocompatible polymer include polyurethane, poly tetra fluoro ethylene (PTFE), fluorinated ethylene propylene (FEP), and poly ether ether ketone (PEEK). The temperature of the core may be raised from 37° C. to a transition temperature of 45-50° C. by the application of DC current (such as DC voltage or radiofrequency) or external energy (such as a magnetic field using clinically available MRI machine or ultrasound using, for example, HIFU). The shape memory element 10" thus changes shape from the straight rod configuration to a curved, coiled or folded configuration.

II. Example Reinforcement Element Delivery Systems

Figure 25:
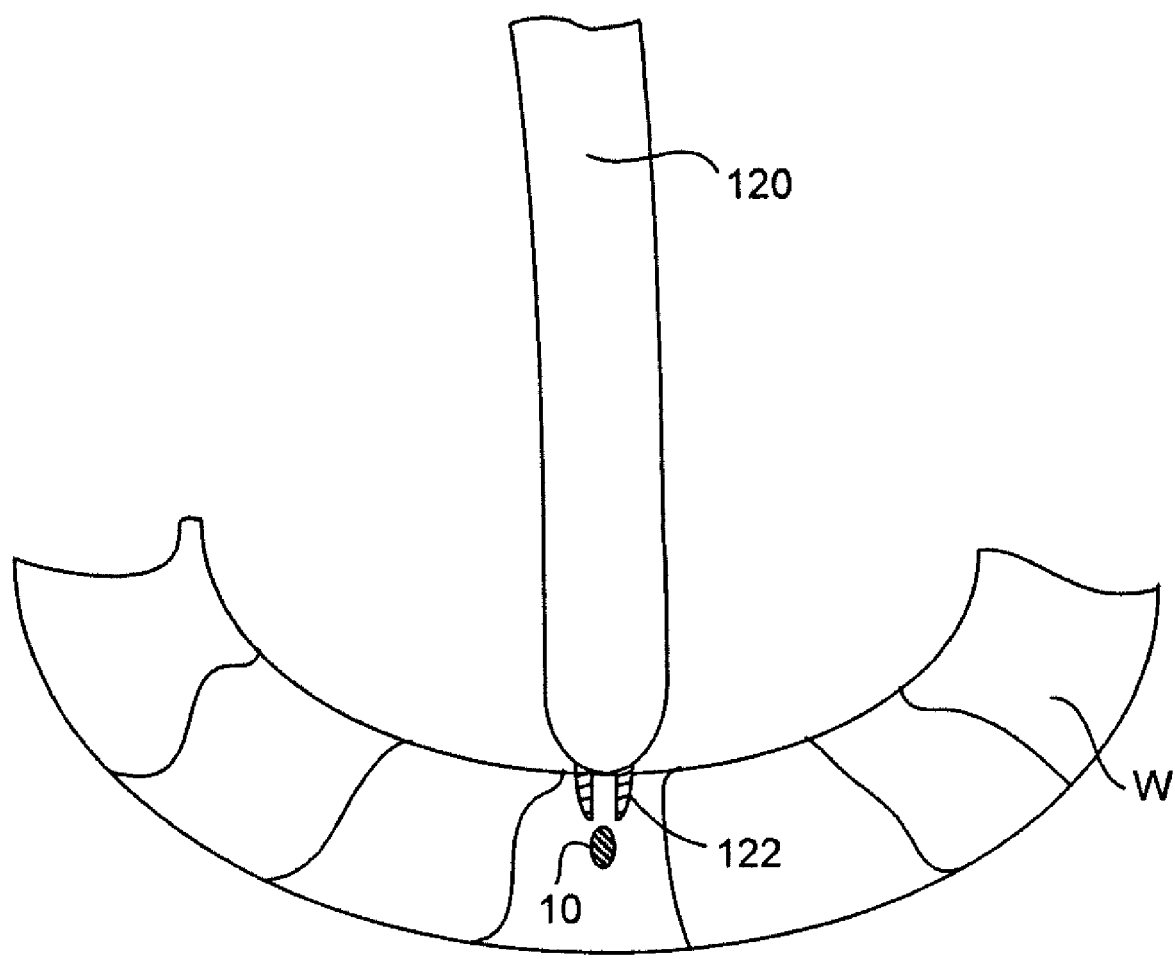
FIG. 25 is a partial cross-sectional view illustrating a reinforcement element being implanted within the heart wall through an open lumen catheter according to one embodiment.

In some embodiments, the reinforcement elements 10 (e.g., the magnetic elements 10' and/or shape memory elements 10") are delivered to the heart wall W through a catheter. For example, FIG. 25 is a partial cross-sectional view illustrating a reinforcement element 10 being implanted within the heart wall W through an open lumen catheter 120 according to one embodiment. The catheter 120 includes an extendable and contractible needle 122 configured to penetrate the heart wall W during implantation. In such an embodiment, the reinforcement element 10 is configured to pass through the needle 122 during implantation. The needle 122 may then be retracted and/or the catheter 120 removed from the patient's body. Although the catheter 120 is represented in FIG. 25 as entering a heart chamber to deliver the reinforcement element 10, in another embodiment, the catheter 120 is used in an epicardial approach to implant the reinforcement element 10 on an outer surface of the heart or within a heart wall W.

Figure 26G:
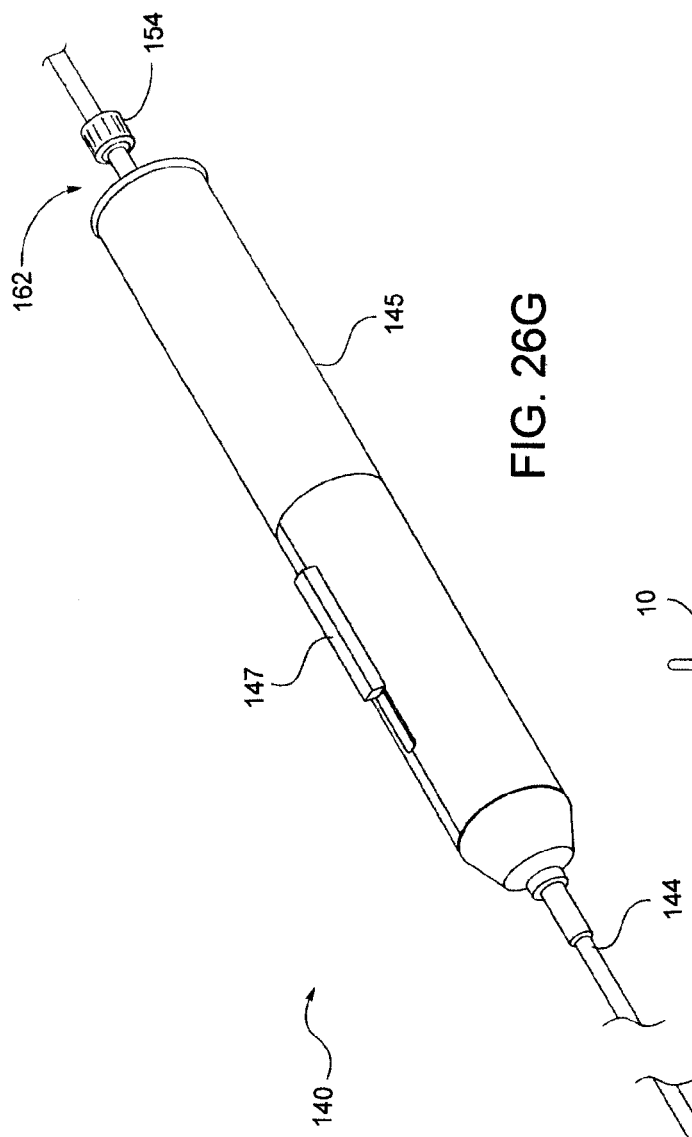
Figure 26H:

In some embodiments, the reinforcement elements 10 are delivered to the heart wall W with the use of an endovascular delivery system. FIGS. 26A-26B illustrate an embodiment of such a delivery system 140. The system 140 includes an elongate catheter 142 having a proximal end 144 attached to a handle 145, a distal end 146, and a lumen 148 extending therethrough. In preferred embodiments, the catheter 142 has an outer diameter in the range of approximately 6-8 French. In addition, the lumen 148 may be sized for passage of a guidewire or for irrigation or contrast media injection. In some embodiments, the lumen 148 is sized for passage of a 0.081-0.035 inch guidewire; for example, the lumen 148 may have an inner diameter (ID) of approximately 0.040 inches or 1 mm. In other embodiments, the lumen 148 has an ID of 1-3 mm.

Typically, the distal end 146 includes a deflectable tip to assist in advancement of the catheter 142 through the vascular anatomy, such as from the femoral or brachial arteries. In some embodiments, the deflectable tip has a functionality similar to the deflectable tips of conventional electrophysiology or percutaneous myocardial revascularization (PMR) catheters. Advancement of the catheter 142 may be visualized with any suitable method, including fluoroscopy. Thus, in some embodiments, the catheter 142 includes a radiopaque marker 149 at the distal tip of the distal end 146. The marker 149 may be comprised of a metal such as gold or platinum. Further, the catheter 142 may be doped with radiopaque material, such as barium sulfate ($BaSO_4$).

Deflection of the catheter 142 may be achieved with the use of pullwires 143. FIG. 26B illustrates a cross-section of the catheter 142 having pullwires 143 extending through walls of the catheter 142 on opposite sides of the lumen 148. The pullwires 143 are manipulated by a deflection knob 147 on the handle 145. Manipulation of the knob 147, such as retraction of the knob 147, applies tension to one of the pullwires 143, which in turn deflects the catheter 142 toward the tensioned pullwire 143, as illustrated in FIG. 26C. FIG. 26D provides a close-up illustration of the curved distal end 146 of the catheter 142. The pullwire 143 may be locked in place, holding the catheter 142 in the deflected position, or the pullwire 143 may be released by advancement of the knob 147 back to a neutral position. Further manipulation of the knob 147, such as advancement of the knob 147, applies tension to the opposite pullwire 143, which in turn deflects the catheter 142 in the opposite direction. Again, the pullwire 143 may be locked in place or released. It may be appreciated that any number of pullwires 143 may be used. Typically, the majority of the catheter 142 is comprised of material which provides sufficient flexibility to maneuver through the vascular anatomy yet sufficient stiffness for successful advancement, such as 70A-90A to 55D-75D durometer Pebax, polyurethane or similar material. However, the distal end 146 of the catheter 142 is typically comprised of a more flexible material, such as 35A-60A durometer Pebax, polyurethane, Pellethane™ (Dow Chemical) or similar material. This difference in durometer allows deflection of the distal end 146 of the catheter 142 while maintaining relative rigidity in the remainder of the catheter 142.

Referring to FIGS. 26E-26F, the delivery system 140 includes a needle 150 having a proximal end 151 and a needle tip 152, wherein the needle 150 which extends through the lumen 148 and is extendable and retractable within the lumen 148 by a needle advancement mechanism 154. The mechanism 154 is axially fixed in relation to the handle 145 and engages the needle 150 via threads so that rotation of the mechanism 154 axially displaces the needle 150. In preferred embodiments, the needle tip 152 is advanceable beyond the distal end 146 of the catheter 142 by a stroke distance of approximately 4-10 mm. The needle 150 may be comprised of any suitable material, such as stainless steel or Nitinol®, and may have any diameter suitable for passage through the lumen 148, such as approximately 1-3 mm.

The reinforcement elements 10 are loadable within the needle 150 for delivery to the heart wall W. Needle 150 has a passageway 160 extending from the proximal end 151 to the needle tip 152 so that one or more reinforcement elements 10 loaded into the proximal end 151 can be advanced through the passageway 160 and expelled from the needle tip 152. The passageway 160 may have any suitable size, such as in the range of approximately 0.25-0.6 mm. In some embodiments, the passageway 160 is coated with a PTFE lining to reduce friction during advancement. Coating of the reinforcement elements 10 with a biocompatible polymer, such as PTFE, also reduces friction. Referring to FIGS. 11G-11H, the reinforcement elements 10 may be advanced through the passageway 160 with the use of a stylet 162. In preferred embodiments, the stylet 162 comprises an elongate shaft having a diameter sized to fit within passageway 160 and a length sized to extend from at least the proximal end 151 of the needle 150 to the needle tip 152. Advancement of the stylet 162 pushes a reinforcement element 10 through the passageway 160 and out of the needle tip 152, as illustrated in FIGS. 26I-26J.

In some embodiments, the delivery system 140 includes mechanisms for delivering an electrical current, such as a DC voltage or radiofrequency, directly to the reinforcement elements 10. In the case of DC voltage, the electrical current may be supplied with the use of DC batteries. Such application of current may be used to bend protrusions of the reinforcement elements 10, as described above, to assist in anchoring the elements 10 in the heart wall W.

Figure 27A:
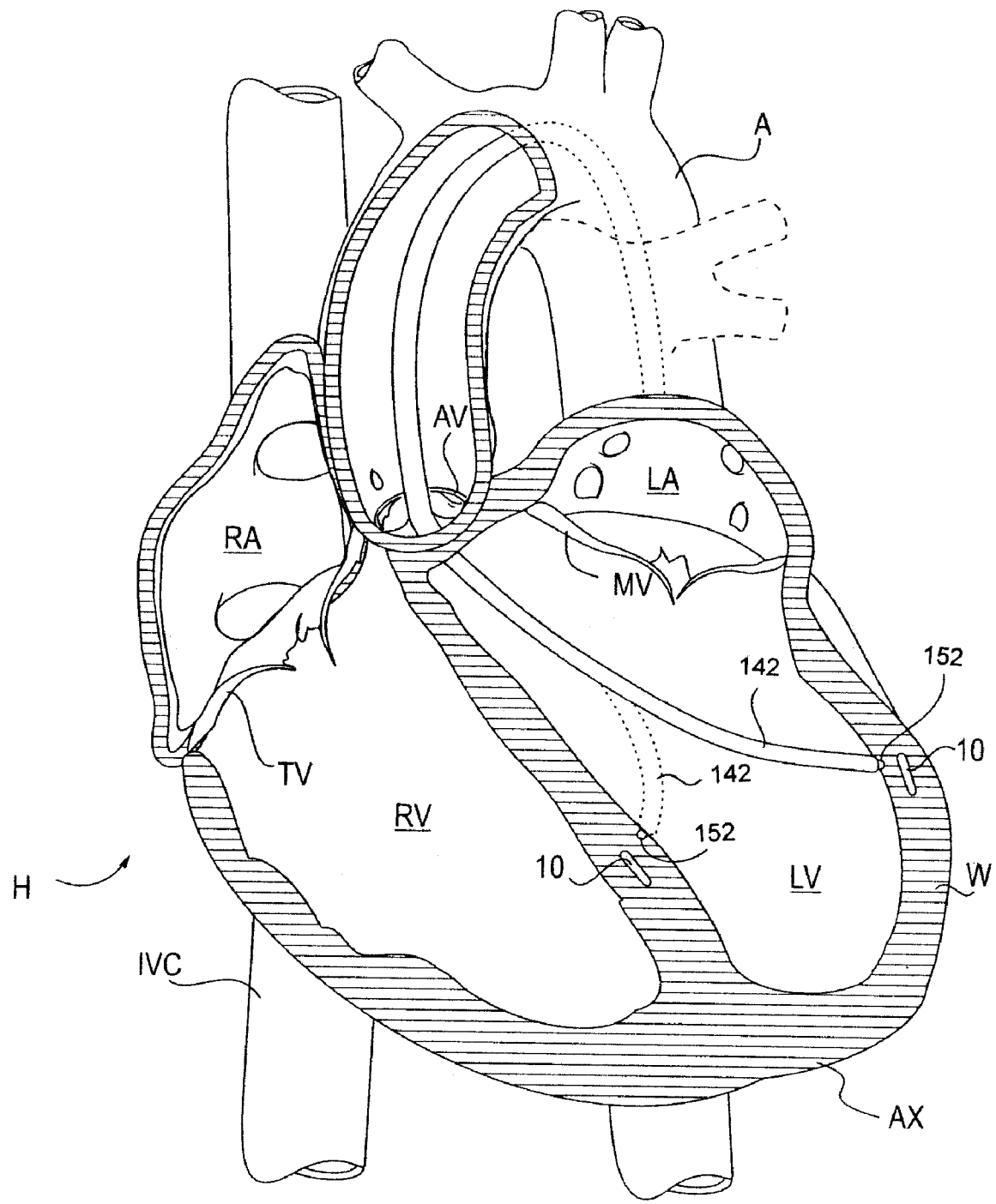
FIG. 27A illustrates an approach for endovascular delivery of reinforcement elements to the walls of the left ventricle according to one embodiment.

FIG. 27 illustrates one approach for endovascular delivery of reinforcement elements 10 to the walls W of the left ventricle LV. Here, a femoral approach is shown wherein the delivery catheter 142 is advanced through the aorta A and the aortic valve AV. Typically, the catheter 142 is advanced through a sheath, such as a 9-10 French sheath, positioned within the femoral artery (not shown). Under fluoroscopy or other methods of guidance, the distal end 146 of the catheter 142 is guided within the left ventricle LV and positioned near or against the ventricular wall W at a target location. After verification of the appropriate positioning of the catheter 142, the needle tip 152 is advanced into the wall W at the target location, as illustrated in FIG. 27. One or more reinforcement elements 10 are then advanced through the needle and out of the needle tip 152 so that the reinforcement element(s) 10 are positioned within the wall W. The catheter 142 may then be repositioned so that the distal end 146 is disposed near or against the ventricular W at another target location, as indicated by dashed image of the catheter. Thus, one or more reinforcement elements 10 may be positioned at other target locations around the left ventricle LV. This may be repeated any number of times.

Figure 27B:
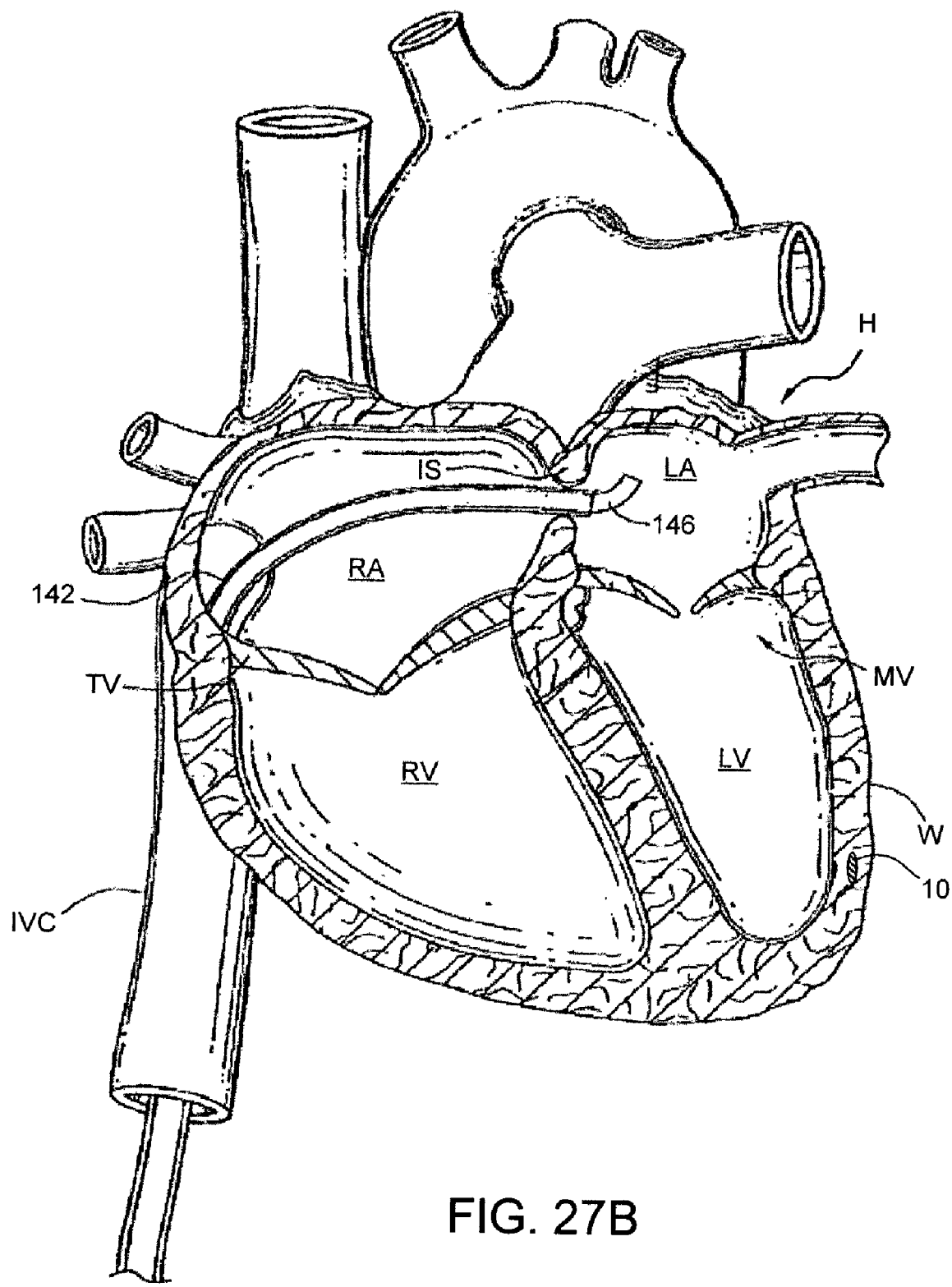
FIG. 27B illustrates another approach for endovascular delivery of reinforcement elements to the heart according to one embodiment.

FIG. 27B illustrates another approach for endovascular delivery of reinforcement elements 10 to the heart H. In this embodiment, the left ventricle LV is approached by advancement of the catheter 142 through the inferior vena cava IVC, into the right atrium RA, across the interatrial septum IS, into the left atrium LA, and through the mitral valve MV.

As shown in FIG. 27B, the catheter 142 is delivered percutaneously into the heart H. A guiding sheath (not shown) may be placed in the vasculature system of the patient and used to guide the catheter 142 and its distal end 146 to a desired deployment site. In some embodiments, a guide wire is used to gain access through the superior or inferior vena cava IVC, for example, through groin access for delivery through the inferior vena cava IVC. The guiding sheath may be advanced over the guide wire and into the inferior vena cava IVC shown in FIG. 27B. The catheter 142 may be passed through the right atrium RA and towards the interatrial septum IS. Once the distal end 146 of the catheter 142 is positioned proximate to the interatrial septum IS, a needle or piercing member is advanced through the catheter 142 and used to puncture the fossa ovalis or other portion of the interatrial septum IS. In some embodiments, the catheter 142 is dimensioned and sized to pass through the fossa ovalis without requiring a puncturing device. That is, the catheter 142 may pass through the natural anatomical structure of the fossa ovalis into the left atrium LA.

Similarly, any chamber (LV, RV, LA, RA) of the heart H may be approached through the inferior vena cava IVC. For example, the right ventricle RV may be approached through the inferior vena cava IVC, into the right atrium RA, and through the tricuspid valve TV. A variety of other endovascular approaches may also be used. It may also be appreciated that non-endovascular approaches may also be used wherein the reinforcement elements 10 are placed on or within the walls W by open chest surgery or through minimally invasive procedures where access is achieved thoracoscopically.

III. Resynchronization Systems and Methods

In one embodiment, the reinforcement elements 10 disclosed herein (e.g., the magnetic elements 10' and/or the shape memory elements 10") are used to reduce or eliminate the shortcomings of conventional cardiac stimulation therapies by providing mechanical booster energy that improves cardiac contraction (EF and CO) during synchronization provided by an external or implantable pulse generator. Thus, an improved or optimal therapy may be provided according to individual patient needs. Using reinforcement elements 10 with cardiac stimulation reduces the number of leads and the amount of energy used to improve cardiac function through resynchronization. Thus, the reinforcement elements 10 increase battery longevity and reduce or minimize the frequency of invasive battery replacement.

A. Resynchronization System Overview

Figure 28:
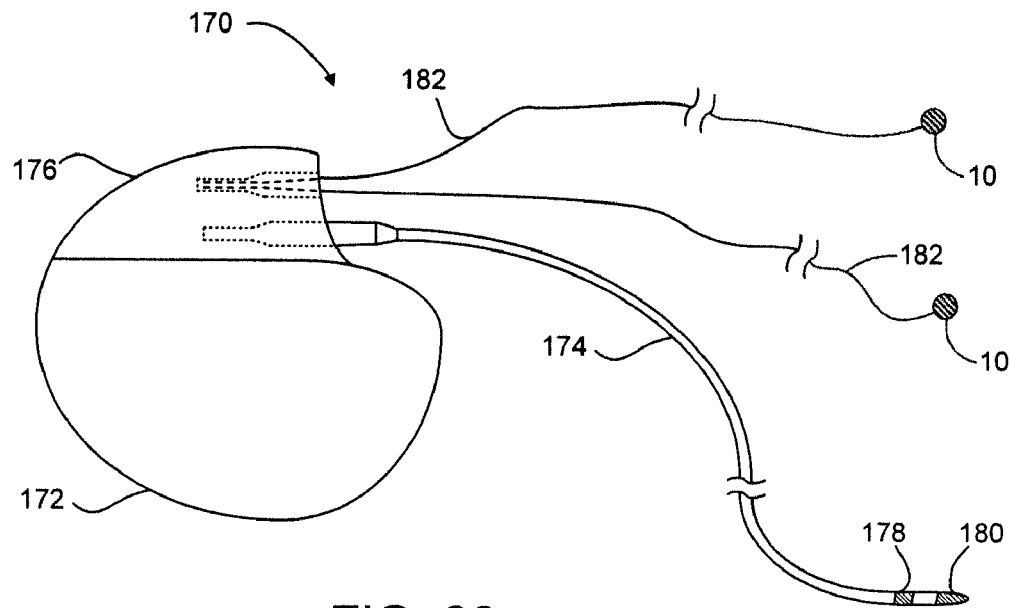
FIG. 28 schematically illustrates a system for improving the hemodynamic efficiency of a heart using cardiac stimulation therapy with mechanical booster energy according to one embodiment.

FIG. 28 schematically illustrates a system 170 for improving the hemodynamic efficiency of a heart using cardiac stimulation therapy with mechanical booster energy according to one embodiment. The system 170 includes an electrical stimulation device 172 configured to deliver an electrical impulse to the heart and at least one reinforcement element 10 (two shown) configured to increase the heart's mechanical energy during the heart's response to the electrical impulse. In some embodiments, the electrical stimulation device 172 includes an implantable pacemaker and/or defibrillator. In other embodiments, the electrical stimulation device 172 may be located external to the patient's body. The electrical stimulation device 172 includes at least one lead 174 configured to deliver the electrical impulse to the heart and/or sense natural or induced depolarizations. The lead 174 is coupled to the stimulation device 172 through a connector block 176.

Figure 29:
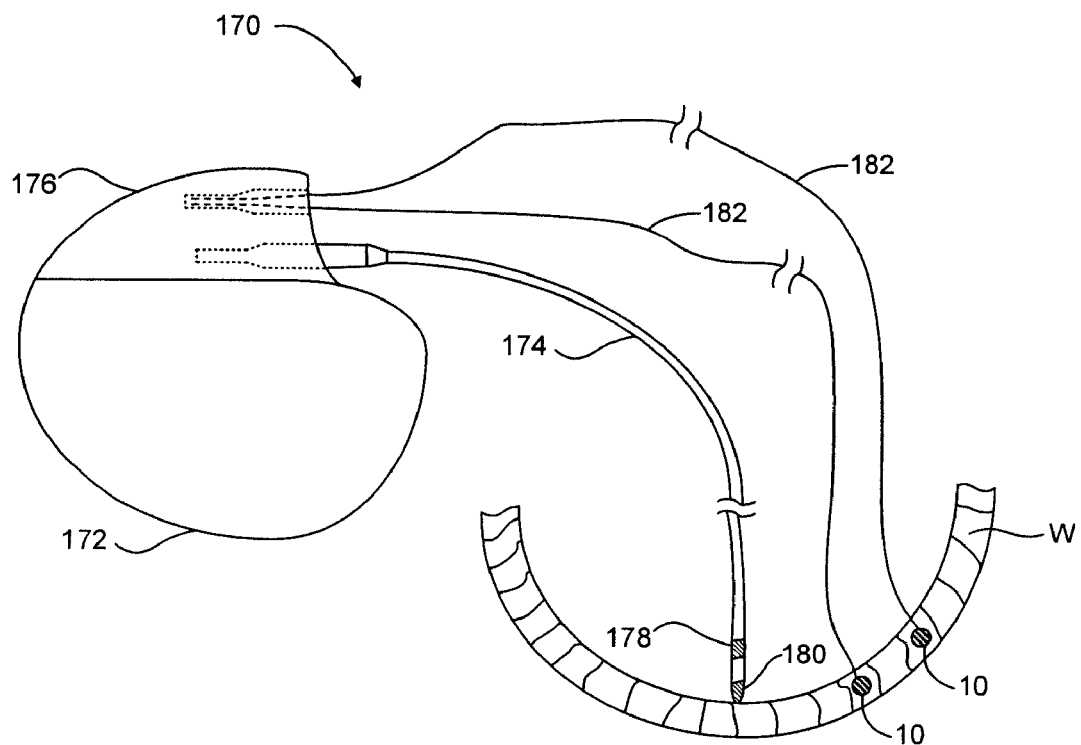
FIG. 29 schematically illustrates the system shown in FIG. 28 with a lead and reinforcement elements implanted in a wall W of the heart according to one embodiment.

FIG. 29 schematically illustrates the system 170 shown in FIG. 28 with the lead 174 and the reinforcement elements 10 implanted in a wall W of the heart according to one embodiment. The reinforcement elements 10 are configured to reshape the wall W of the heart. The reshaped or contracted wall W of the heart provides mechanical booster energy that increases the heart's pumping efficiency. The reinforcement elements 10 may include either the magnetic elements 10' or shape memory elements 10" discussed herein. In one embodiment, a combination of magnetic elements 10' and shape memory elements 10" are used to reshape the heart to provide the mechanical booster energy. Although the reinforcement elements 10 are shown as being round in FIGS. 28-31 and 33-34, an artisan will recognize from the disclosure herein that the reinforcement elements 10 may be discs, cones, rods, blocks, spheres, rings, or any other suitable shape.

Figure 30:
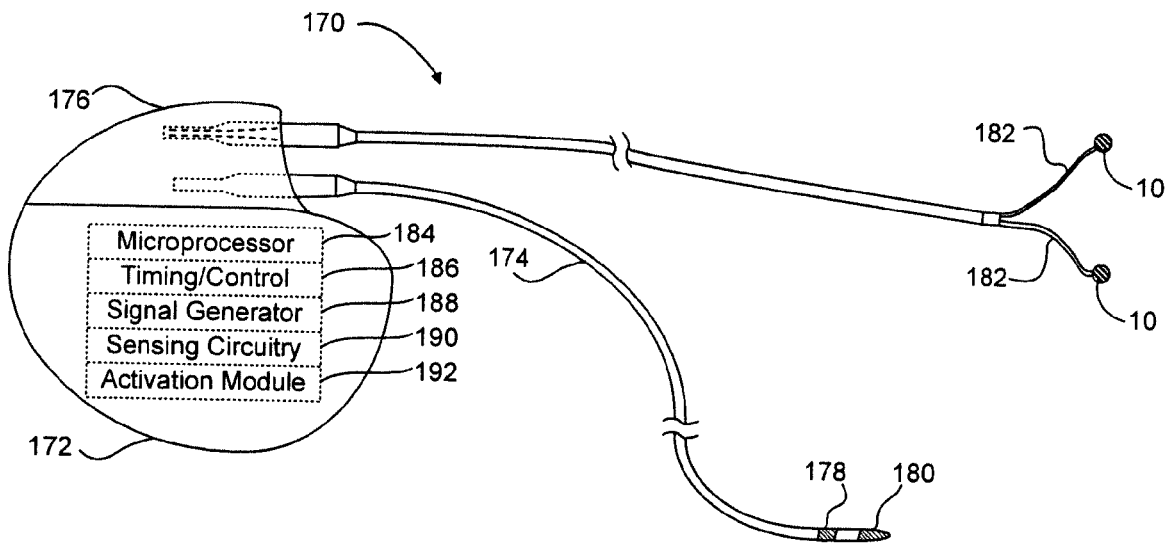
FIG. 30 illustrates a block diagram of the electrical stimulation device shown in FIG. 28 according to one embodiment.
Figure 31:
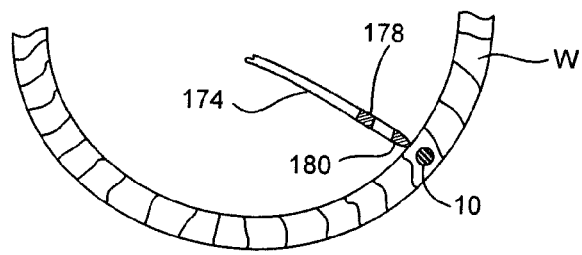
FIG. 31 illustrates a lead positioned proximate to a reinforcement element according to one embodiment.

FIG. 30 illustrates a block diagram of the electrical stimulation device 172 shown in FIG. 28 according to one embodiment. In this example embodiment, the electrical stimulation device 172 includes a microprocessor 184, timing/control circuitry 186, a signal generator 188, sensing circuitry 190, and an activation module 192. The microprocessor 184 may include, for example, one or more controllers, program logic, software, hardware or other substrate configurations capable of representing data and instructions that operate as described herein or similar thereto. The microprocessor 184 may also include controller circuitry, processor circuitry, general purpose single-chip or multi-chip microprocessors, digital signal processors, embedded microprocessors, microcontrollers, combinations of the foregoing, or the like.

The timing/control circuitry 186 is configured to trigger the signal generator 188 to generate an electrical impulse for pacing/defibrillation. The timing/control circuitry 186 may trigger the signal generator 188 at predetermined time intervals corresponding to a pacing rate. As discussed in more detail below, in some embodiments, the timing/control circuitry 186 may also adjust the time interval between electrical impulses based on signals received by the sensing circuitry 190.

The activation module 192 is configured to generate a magnetic field or to provide activation energy to the one or more reinforcement elements 10 to initiate a shape change in a shape memory material. For example, in a magnetic embodiment, the activation module 192 may selectively control one or more electromagnets to generate an electric field such that two or more reinforcement elements 10 attract each other so as to contract the heart muscle. As another example, in embodiments wherein the reinforcement elements 10 include shape memory material, the lead 174 may be placed in close proximity to the reinforcement element 10 (see FIG. 31) so as to provide sufficient activation energy to cause the reinforcement element 10 to transition from a first shape to a second shape after implantation, as discussed above. The activation energy may include, for example, thermal energy, electrothermal energy (e.g., via electric current), electromagnetic energy, electromechanical energy, sonic energy (e.g., HIFU), RF energy, or other forms of energy.

B. Lead/Reinforcement Element Placement Based on Cardiac Band Theory

In one embodiment, pacemaker/defibrillator leads and/or reinforcement elements are implanted within or on the heart at locations that take advantage of a band theory model of the heart. Placement based on cardiac band theory creates a more physiological contraction pattern and heart motion.

Generally, it has been proposed that the ventricular myocardium, both right ventricle (RV) and left ventricle (LV), exists as a continuous muscle band. The band is oriented spatially as a helix formed by basal and apical loops. This unique anatomy and spatial configuration of the myocardial muscle determine the way that the ventricular ejection and filling take place.

Movements of the heart in cine-loop nuclear magnetic resonance studies of normal individuals demonstrates a lack of movement of the apex during the cardiac cycle. Instead, the entire base of the heart (atria and great vessels) move downward in systole and upward in diastole. Such studies demonstrate a new model of heart structure. Thus, in certain embodiments disclosed herein, synchronization therapy includes strategic placement of reinforcement implants at specific locations within the left ventricle to reshape a portion of the left ventricle so as to provide mechanical booster energy to the heart during electrical stimulation thereof. For example, reinforcement elements implanted within the left ventricle may be located around the septal wall, the lower portion of the free wall, and/or the apex of the heart. Such embodiments enhance contractility and create a more physiological response to pacing/defibrillation.

C. System Leads

Figure 32:
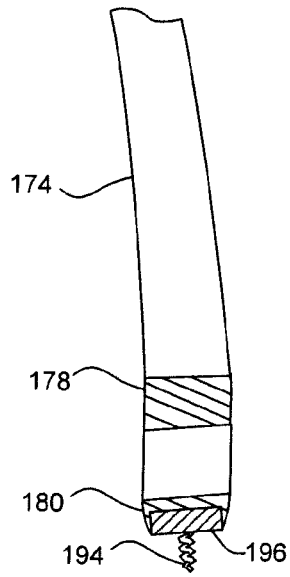
FIGS. 32-34 illustrate leads according to certain embodiments.
Figure 33:
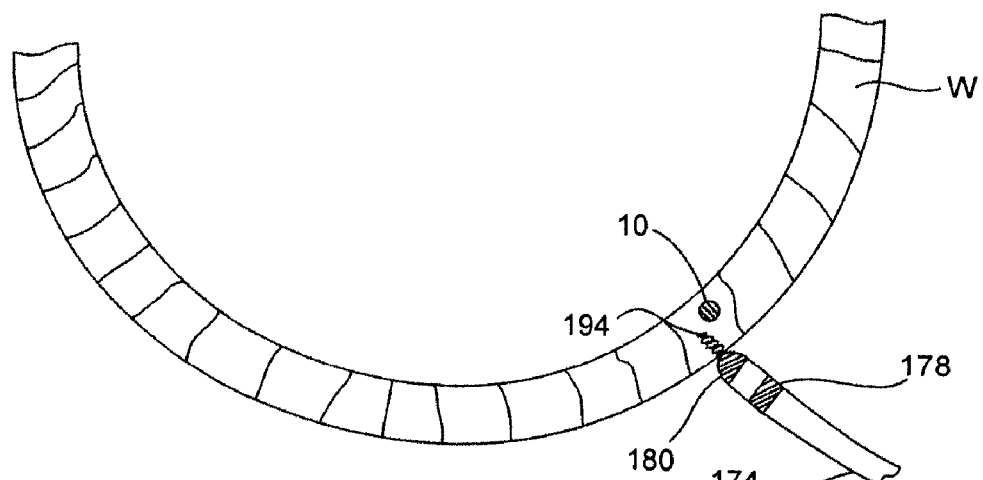
Figure 34:
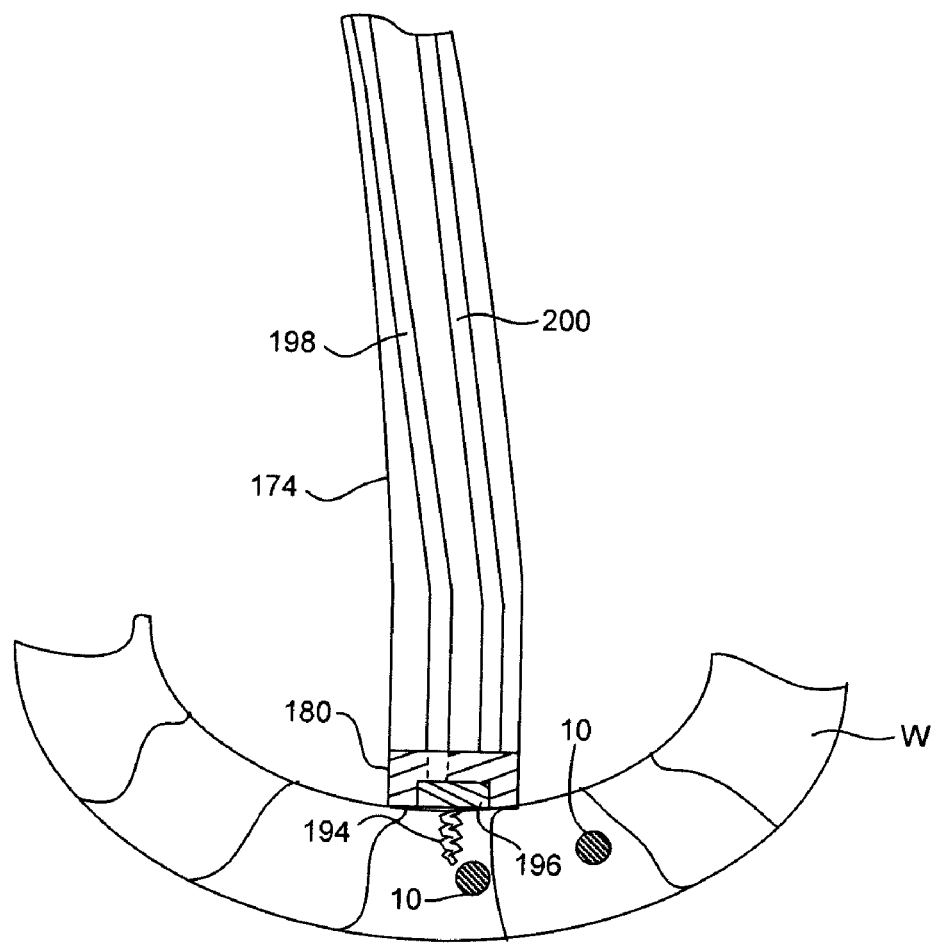

In one embodiment, the lead 174 includes a bipolar endocardial lead generally used with implantable or external pacemakers. The lead 174 includes a ring electrode 178 and a tip electrode 180 for delivering the electrical impulses to the heart (e.g., from the signal generator 188 shown in FIG. 30) and/or for sensing depolarizations (e.g., using the sensing circuitry 190 shown in FIG. 30). As shown in FIGS. 32-34, in some embodiments the lead 174 also includes a screw-in tip 194 configured to attach the lead 174 to the wall W of the heart muscle.

The lead 174 may also be configured in some embodiments to deliver activation energy (e.g., from the activation module 192 shown in FIG. 30) to the reinforcement elements 10 to initiate a shape change in a shape memory material. For example, FIGS. 32 and 34 schematically illustrate an activation electrode 196 located within the tip electrode 180 of the lead 174 and configured to deliver the activation energy to one or more of the reinforcement elements 10. The activation electrode 196 may be configured to make contact with a tissue area of the wall W of the heart muscle that is sufficiently close to the reinforcement element 10 so as to efficiently deliver the activation energy thereto. Although not shown, in other embodiments, the activation electrode 196 is not located within the tip electrode 180. For example, the activation electrode 196 may be located between the ring electrode 178 and the tip electrode 180, within the ring electrode 178, or at another location on the lead 174.

As schematically illustrated in FIG. 34, the lead 174 may include an electrical conductor 198 configured to couple the activation electrode 196 to the activation module 192 shown in FIG. 30. In one such embodiment, the lead 174 also includes another electrical conductor 200 configured to couple the tip electrode 180 to the signal generator 188. Thus, the activation energy and the pacing/defibrillation impulses may be independently controlled. In other embodiments, the activation energy and the pacing/defibrillation impulses are provided through the same electrical conductor/electrode. For example, the pacing/defibrillation impulses may be configured to provide the activation energy to the reinforcement elements 10.

In some embodiments, the activation electrode 196 may also be configured to sense electromagnetic energy, electrothermal energy, electromechanical energy, a combination of the foregoing, and/or other forms of energy. The microprocessor 184 shown in FIG. 30 may use data related to the sensed energy to adjust pacing pulses in order to compensate for heart wall motion and contractility, thereby improving ejection fraction and cardiac output. In one embodiment, the energy sensed by the activation electrode 196 provides feedback to the activation module 192 to allow precise control of the amount of activation energy delivered to the reinforcement elements 10. Thus, the activation module 192 may control the amount of mechanical booster energy (e.g., through partial and/or reversible shape change of shape memory material). In addition, or in other embodiments, the energy sensed by the activation electrode 196 may be used to measure distance data related to the ventricular contraction and relaxation phases of the heart cycle. For example, in one embodiment, the activation electrode 196 may sense variations in a magnetic field as the activation electrode 196 moves toward and away from a magnetic implant (e.g., a magnetic element 10') during the heart cycle. Thus, the measured variations in the magnetic field may be used to determine the mechanical performance of the ventricles.

As shown in FIGS. 28-30, the system 170 according to certain embodiments also includes one or more leads 182 (two shown) configured to provide a connection between the electrical stimulation device 172 and the respective reinforcement elements 10. In such embodiments, the reinforcement elements 10 are configured as electrodes for sensing depolarizations and/or for providing electrical impulses to the heart for pacing/defibrillation. For example, in one embodiment, the reinforcement elements 10 sense electrical signals in the heart (e.g., electrocardiogram signals) including at least one QRS complex that may be used to diagnose heart conditions and/or to provide feedback for improving pacing therapy. By acting as both reinforcement devices and sensing electrodes, the overall number of implants/leads is reduced.

Signals sensed through the reinforcement elements 10 may also be used to determine distance data related to the motion of the beating heart muscle. For example, in a contraction measurement mode, signals sensed by the reinforcement elements 10 at two different sites in the heart are monitored and assessed during the ventricular contraction and relaxation phases of the heart cycle. The signals sensed from the two different sites are indicative of the mechanical performance of the ventricles. In one embodiment, a first ventricular site includes a right ventricular (RV) pace/sense electrode site, and a second ventricular site includes a left ventricular (LV) pace/sense electrode site. In one such embodiment, an intracardiac electrogram is sensed in terms of its amplitude and slew rate (e.g., rate of change/time). The intra-cardiac elctrogram is used as closed-loop sensing to automatically adjust a pacing rate.

As another example, in a rate responsive mode, the mechanical performance of the ventricles is assessed from measured distance data determined from signals sensed by the reinforcement elements 10 to provide measurements of stroke volume (as derived from cardiac displacement), contractility, or ejection fraction (which, as discussed above, is related to stroke volume). These measurements may be used to control the electrical pulses delivered to the heart to provide hemodynamically optimal pacing therapy.

Thus, the electrical stimulation and sensing provided by the systems and methods disclosed herein may be employed in, for example, assessment of electromechanical dissociation and cardiac output during pacing or arrhythmias, mechanical confirmation of capture or loss of capture for auto capture algorithms (e.g., algorithms that automatically assess pacing threshold and adjust pacing output to improve or ensure consistent myocardial capture), optimization of multisite pacing for heart failure, rate responsive pacing based on myocardial contractility, automatic adjustment of sense amplifier sensitivity based on detection of mechanical events, determination of pacemaker mode switching, and determination of the need for fast and aggressive versus slower and less aggressive antitachyarrhythmia therapies. Other uses of electrical stimulation and/or sensing will occur to those of ordinary skill in the art from reading the disclosure herein.

In some embodiments, the leads 182 may also be configured to deliver activation energy to the reinforcement elements 10 to initiate a shape change in a shape memory material or to generate a magnetic field. For example, in one embodiment, the reinforcement elements 10 include passive elements that may be selectively magnetized and demagnetized (e.g., electromagnets that create a magnetic field when current is passed therethrough via the respective leads 182) as the pacing lead 174 delivers electrical pulses to the heart. Thus, the reinforcement elements 10 may repeatedly contract and relax the wall W of the heart to provide mechanical booster energy that is synchronized with the electrical stimulation of the heart. As another example, the leads 182 may be used to initiate a shape change in a shape memory material, as discussed herein.

While certain embodiments have been described herein in detail, these embodiments have been described by way of example only, and are not intended to limit the scope of the inventions. Indeed, the novel systems and methods described herein may be embodied in a variety of other forms; furthermore, various omissions, substitutions and changes in the form of the methods and systems described herein may be made without departing from the spirit of the inventions. The scope of the disclosed embodiments should, therefore, be determined only by the following claims.

The invention claimed is:

1. A method for improving the hemodynamic efficiency of a heart, the method comprising:
    implanting at least one reinforcement element within a wall of the heart; and
    electrically stimulating the heart;
    wherein the at least one reinforcement element is configured to increase the heart's mechanical energy during a response to the electrical stimulation.

2. The method of claim 1, further comprising:
    detecting electrocardiogram signals through the at least one reinforcement element implanted within the wall of the heart; and
    based on the detected electrocardiogram signals, controlling delivery of an electrical impulse configured to provide the electrical stimulation.

3. The method of claim 1, further comprising delivering an electrical impulse through the at least one reinforcement element implanted within the wall of the heart, the electrical impulse configured to provide the electrical stimulation to the heart.

4. The method of claim 3, further comprising selectively delivering the electrical impulse based on a detected signal related to the mechanical motion of the heart.

5. The method of claim 1, further comprising, after implantation, delivering sufficient activation energy to the at least one reinforcement element to change a configuration of the at least one reinforcement element, wherein the activation energy is selected from the group comprising thermal energy, a magnetic energy, acoustic energy, and electromagnetic energy.

6. The method of claim 1, further comprising implanting the at least one reinforcement element through at least one of a percutaneous approach within the heart, an epicardial approach from outside of the heart, and an open lumen catheter with an extendible and retractable hollow needle.

7. A system for improving the hemodynamic efficiency of a heart, the system comprising:
    an electrical stimulation device configured to deliver an electrical impulse to the heart;
    at least one reinforcement element implantable at least partially within a tissue area of the heart, the at least one reinforcement element configured to increase the heart's mechanical energy during a response to the electrical impulse; and
    a lead electrically coupled to the electrical stimulation device, the lead comprising:
        a first electrode configured to deliver the electrical impulse to a tissue area of the heart; and
        a second electrode configured to deliver activation enerqy to the at least one reinforcement element,
        wherein the first electrode is located in a tip of the lead and the second electrode is located within a recess of the first electrode such that both the first and second electrode contact the tissue area of the heart in close proximity to the at least one reinforcement element.

8. The system of claim 7, wherein the at least one reinforcement element is configured to attach to a surface of the heart.

9. The system of claim 7, wherein the electrical stimulation device is selected from the group comprising a pacemaker and a defibrillator.

10. The system of claim 7, wherein the at least one reinforcement element comprises a shape memory material, the shape memory material being transitionable between an original shape and at least one memory shape, wherein the original shape is configured for at least partial implantation within the tissue area of the heart, and wherein the at least one memory shape is configured to apply force to the tissue area of the heart in order to reshape the tissue area of the heart after receiving sufficient activation energy.

11. The system of claim 10, wherein the electrical stimulation device is configured to deliver the activation energy to the at least one reinforcement element, the activation energy selected from the group comprising thermal energy, magnetic fields, acoustic energy, and electromagnetic energy.

12. The system of claim 10, wherein the shape memory material comprises a shape memory polymer.

13. The system of claim 10, wherein the shape memory material comprises a shape memory metal or metal alloy.

14. The system of claim 13, wherein the shape memory metal or metal alloy is configured to exhibit a paramagnetic or ferromagnetic transition.

15. The system of claim 7, further comprising:
   diagnostic circuitry configured to analyze depolarizations within the heart; and
   an electrode electrically connected to the diagnostic circuitry, the electrode configured to sense the depolarizations within the heart,
   wherein the electrical simulation device is configured to stimulate the heart based on the sensed depolarizations.

16. The system of claim 15, wherein the diagnostic circuitry is configured to coordinate at least one of an output signal magnitude and a rate of change of magnitude with heart contraction and ejection fraction values.

17. The system of claim 7, wherein the lead further comprises a screw-in tip to secure the lead to the tissue area of the heart.

18. The system of claim 7, wherein the at least one reinforcement element comprises at least one magnetic element.

19. The system of claim 18, wherein the at least one magnetic element comprises a magnetic core comprising at least one of Neudynium Iron Boron, Samarium Cobalt, and Aluminum Nickel Cobalt.

20. A system comprising:
   means for electrically stimulating a patient's heart; and
   means for reshaping the heart to increase the heart's mechanical energy during a response to the electrical stimulation, the means for reshaping the heart configured to be implanted within a wall of the heart.

21. The system of claim 20, wherein the means for reshaping the heart is configured to sense depolarizations within the patient's heart, and wherein the means for electrically stimulating the heart provides an electrical impulse based on the sensed depolarizations.

22. The system of claim 20, wherein the means for reshaping the heart is configured to deliver an electrical impulse provided by the means for electrically stimulating the patient's heart.

* * * * *